US012797305B2

(12) United States Patent
Reynolds

(10) Patent No.: US 12,797,305 B2
(45) **Date of Patent: *Nov. 17, 2026**

(54) FLUORIDE COMPOSITION AND METHODS FOR DENTAL MINERALIZATION

(71) Applicant: THE UNIVERSITY OF MELBOURNE, Parkville (AU)

(72) Inventor: Eric Charles Reynolds, Carlton (AU)

(73) Assignee: THE UNIVERSITY OF MELBOURNE, Parkville (AU)

( * ) Notice: Subject to any disclaimer, the term of this patent is extended or adjusted under 35 U.S.C. 154(b) by 897 days.

This patent is subject to a terminal disclaimer.

(21) Appl. No.: 18/052,390

(22) Filed: Nov. 3, 2022

(65) Prior Publication Data

US 2024/0000671 A1 Jan. 4, 2024

Related U.S. Application Data

(63) Continuation of application No. 15/609,564, filed on May 31, 2017, now Pat. No. 11,504,305, which is a continuation of application No. 12/162,683, filed as application No. PCT/AU2007/000141 on Feb. 9, 2007, now Pat. No. 9,668,945.

(30) Foreign Application Priority Data

Feb. 9, 2006 (AU) ................................ 2006900634
Jun. 30, 2006 (AU) ................................ 2006903531

(51) Int. Cl.

| | |
|---|---|
| ***A61K 6/838*** | (2020.01) |
| ***A61G 11/00*** | (2006.01) |
| ***A61K 8/21*** | (2006.01) |
| ***A61K 8/24*** | (2006.01) |
| ***A61Q 11/00*** | (2006.01) |

(52) U.S. Cl.

CPC .............. *A61K 6/838* (2020.01); *A61G 11/00* (2013.01); *A61K 8/21* (2013.01); *A61K 8/24* (2013.01)

(58) Field of Classification Search

CPC .................................. A61K 8/24; A61Q 11/00
USPC ........................................................... 424/49
See application file for complete search history.

(56) References Cited

U.S. PATENT DOCUMENTS

| | | | |
|---|---|---|---|
| 3,864,471 | A | 2/1975 | King et al. |
| 3,966,901 | A | 6/1976 | Cullum et al. |
| 4,080,440 | A | 3/1978 | Digiulio et al. |
| 4,157,386 | A | 6/1979 | La Rochelle |
| 4,357,318 | A | 11/1982 | Shah et al. |
| 4,522,805 | A | 6/1985 | Gordon |
| 4,588,763 | A | 5/1986 | Brannstrom et al. |
| 4,672,032 | A | 6/1987 | Slavkin et al. |
| 5,015,628 | A | 5/1991 | Reynolds |
| 5,227,154 | A | 7/1993 | Reynolds |
| 5,427,769 | A | 6/1995 | Berrocal et al. |
| 5,447,732 | A | 9/1995 | Tanimoto et al. |
| 5,520,725 | A | 5/1996 | Kato et al. |
| 5,833,953 | A | 11/1998 | Berrocal et al. |
| 5,981,475 | A | 11/1999 | Reynolds |
| 6,036,944 | A | 3/2000 | Winston et al. |
| 6,056,930 | A | 5/2000 | Tung |
| 6,120,754 | A | 9/2000 | Lee et al. |
| 6,149,894 | A | 11/2000 | Yamane et al. |
| 6,214,101 | B1 | 4/2001 | Nakaseko |
| 6,652,875 | B1 | 11/2003 | Bannister |
| 6,780,844 | B1 | 8/2004 | Reynolds |
| 7,312,193 | B2 | 12/2007 | Reynolds |
| 7,491,694 | B2 | 2/2009 | Reynolds et al. |
| 8,603,988 | B2 | 12/2013 | Reynolds |
| 8,609,071 | B2 | 12/2013 | Reynolds |
| 8,673,363 | B2 | 3/2014 | Reynolds |
| 9,295,628 | B2 | 3/2016 | Reynolds |
| 9,668,945 | B2 | 6/2017 | Reynolds |
| 10,695,370 | B2 | 6/2020 | Reynolds |
| 10,912,722 | B2 | 2/2021 | Reynolds |
| 11,351,193 | B2 | 6/2022 | Reynolds |
| 11,504,305 | B2 | 11/2022 | Reynolds |
| 11,564,873 | B2 | 1/2023 | Reynolds |
| 11,717,536 | B2 | 8/2023 | Reynolds |
| 11,717,537 | B2 | 8/2023 | Reynolds |
| 12,128,068 | B2 | 10/2024 | Reynolds |
| 2002/0028251 | A1 | 3/2002 | Okay |
| 2002/0071858 | A1 | 6/2002 | Luo et al. |
| 2003/0124066 | A1 | 7/2003 | Dixon et al. |
| 2003/0152525 | A1 | 8/2003 | Dixon, Jr. et al. |
| 2003/0165442 | A1 | 9/2003 | Baig et al. |
| 2005/0063922 | A1 | 3/2005 | Reynolds et al. |
| 2005/0089481 | A1 | 4/2005 | Yamanaka et al. |

(Continued)

FOREIGN PATENT DOCUMENTS

| | | | |
|---|---|---|---|
| AU | 718253 | B2 | 7/1997 |
| CN | 104001157 | A | 8/2014 |

(Continued)

OTHER PUBLICATIONS

CDC, "Recommendations for Using Fluoride to Prevent and Control Dental Caries in the United States." MMWR; Aug. 17, 2001/ vol. 50/No. RR14 (Year: 2001).*

Fernando et al., "Self-assembly of dental surface nanofilaments and remineralisation by SnF2 and CPP-ACP nanocomplexes", Sci Rep, 2019; 9: 1285.

Gurunathan D et al., "Casein phosphopeptide-amorphous calcium phosphate: a remineralizing agent of enamel", Australian Dental Journal, 2012; 57: 404-408.

Ajaj et al., "Effect of different acid etchants on the remineralization process of white-spot lesions: An in vitro study.", American Journal of Dentistry, Feb. 2020; pp. 43-47.

Hsu C.-Y.S. et al., "Laser-Matrix-Fluoride Effects on Enamel Demineralization", Journal of Dental Research, Sep. 2001; vol. 80, No. 9, pp. 1797-1801.

(Continued)

*Primary Examiner* — Walter E Webb
(74) *Attorney, Agent, or Firm* — Foley & Lardner LLP

(57) ABSTRACT

The present invention relates to compositions and methods for mineralizing a dental surface or subsurface including providing a composition including stabilized ACP and a source of fluoride ions.

7 Claims, No Drawings

Specification includes a Sequence Listing.

(56) References Cited

U.S. PATENT DOCUMENTS

| | | | |
|---|---|---|---|
| 2005/0100581 | A1 | 5/2005 | Laurencin et al. |
| 2005/0118115 | A1 | 6/2005 | Fontenot |
| 2006/0183081 | A1 | 8/2006 | Bevilacqua et al. |
| 2007/0254260 | A1 | 11/2007 | Alden et al. |
| 2008/0075675 | A1 | 3/2008 | Reynolds |
| 2008/0171001 | A1 | 7/2008 | Engelman et al. |
| 2008/0193557 | A1 | 8/2008 | Reynolds |
| 2009/0016972 | A1 | 1/2009 | Manasherov et al. |
| 2009/0022672 | A1 | 1/2009 | Reynolds |
| 2009/0324662 | A1 | 12/2009 | Kutsch et al. |
| 2010/0028273 | A1 | 2/2010 | Fischer et al. |
| 2011/0076241 | A1 | 3/2011 | Kato et al. |
| 2012/0100194 | A1 | 4/2012 | Yamai et al. |
| 2012/0129135 | A1 | 5/2012 | Yang et al. |
| 2013/0129641 | A1 | 5/2013 | Sadeghpour et al. |
| 2014/0147512 | A1 | 5/2014 | Reynolds |
| 2016/0158283 | A1 | 6/2016 | Reynolds |
| 2016/0317404 | A1 | 11/2016 | Reynolds |
| 2017/0333296 | A1 | 11/2017 | Reynolds |
| 2018/0008518 | A1 | 1/2018 | Reynolds |
| 2020/0054672 | A1 | 2/2020 | Reynolds |
| 2020/0197486 | A1 | 6/2020 | Reynolds |
| 2020/0246378 | A1 | 8/2020 | Reynolds |
| 2021/0161778 | A1 | 6/2021 | Reynolds |
| 2022/0142881 | A1 | 5/2022 | Reynolds |
| 2022/0183810 | A1 | 6/2022 | Reynolds |
| 2023/0404867 | A1 | 12/2023 | Reynolds |
| 2024/0016836 | A1 | 1/2024 | Reynolds |

FOREIGN PATENT DOCUMENTS

| | | | |
|---|---|---|---|
| CN | 1040011574 | A | 8/2014 |
| EA | 011125 | B1 | 12/2008 |
| EP | 0 786 245 | A1 | 7/1997 |
| EP | 1 525 878 | A1 | 4/2005 |
| EP | 1 952 801 | A1 | 8/2008 |
| EP | 2 301 513 | A2 | 3/2011 |
| EP | 2 353 576 | A1 | 8/2011 |
| JP | H08-026925 | A | 1/1996 |
| JP | 08-143436 | A | 6/1996 |
| JP | H08-143436 | A | 6/1996 |
| JP | 10-290682 | A | 11/1998 |
| JP | H11-228327 | A | 8/1999 |
| JP | 11-310599 | A | 11/1999 |
| JP | 3742523 | | 11/1999 |
| JP | H11-310599 | A | 11/1999 |
| JP | 2002-338447 | | 11/2002 |
| JP | 2004-215521 | A | 8/2004 |
| JP | 2005-112841 | A | 4/2005 |
| JP | 2010-047494 | A | 3/2010 |
| JP | 2011-032250 | A | 2/2011 |
| JP | 2013-163656 | A | 8/2013 |
| WO | WO-82/03008 | A1 | 9/1982 |
| WO | WO-87/07615 | | 12/1987 |
| WO | WO-93/03707 | | 3/1993 |
| WO | WO-94/00146 | A1 | 1/1994 |
| WO | WO-96/29340 | A1 | 9/1996 |
| WO | WO-97/36943 | A1 | 10/1997 |
| WO | WO-97/40811 | A1 | 11/1997 |
| WO | WO-98/40406 | A1 | 9/1998 |
| WO | WO-99/471089 | | 9/1999 |
| WO | WO-00/06108 | A1 | 2/2000 |
| WO | WO-00/57842 | A1 | 10/2000 |
| WO | WO-00/57842 | A2 | 10/2000 |
| WO | WO-00/57892 | | 10/2000 |
| WO | WO-01/44106 | A1 | 6/2001 |
| WO | WO-02/094204 | A1 | 11/2002 |
| WO | WO-03/059303 | A2 | 7/2003 |
| WO | WO-03/059304 | A1 | 7/2003 |
| WO | WO-03/099234 | | 12/2003 |
| WO | WO-2004/035077 | A1 | 4/2004 |
| WO | WO-2004/054531 | A1 | 7/2004 |
| WO | WO-2004/060336 | A1 | 7/2004 |
| WO | WO-2006/056013 | A1 | 6/2006 |
| WO | WO-2006/130913 | A1 | 12/2006 |
| WO | WO-2006/135982 | A1 | 12/2006 |
| WO | WO-2007/090242 | A1 | 8/2007 |
| WO | WO-2009/130447 | A1 | 10/2009 |
| WO | WO-2010/134904 | A1 | 11/2010 |
| WO | WO-2015/010166 | A1 | 1/2015 |
| WO | WO-2015/095932 | A1 | 7/2015 |
| WO | WO-2016/101041 | A1 | 6/2016 |

OTHER PUBLICATIONS

Huang et al., "Remineralisation Effect of CPP-ACP and Diode Laser Stabilised by Case on the Initial Enamel caries of Primary Teeth", Progress in Modern Biomedicine, Jan. 2019; 19(2): 279.

Kshirsagar et al., "Comparative assessment of bond strengths of affected dentin, using two different remineralizing solutions with or without lasers: Results of an in vitro pilot study", SRM Journal of Research in Dental Sciences, Jan. 2015; vol. 6, No. 2.

L.J. Walsh "Clinical applications of Recaldent products: which ones to use where," Australasian Dental Practice, May/Jun. 2007, 144-146. (Year: 2007).

Sakr, A. K., ELkarargy, A. A. M., & Sherif, M. M. (2007). The Effect of Recaldent (CPP-ACP) on the most putative bacteria in caries and chronic gingivitis. Ain Shams Dental Journal, 211-219. (Year: 2007).

Verguard et al., "Mineral-binding milk proteins and peptides; occurrence, biochyemical and technological characteristics", British Journal of Nutrition, Nov. 2000; 84: Suppl. 1, S91-S98.

White, A return to stannous fluoride dentrifices, Journal of clinical dentistry, Feb. 1995; Spec No. 29-36.

A. L. Boskey and A. S. Posner. "Conversion of Amorphous Calcium Phosphate to Microcrystalline Hydroxyapatite. A pH-Dependent, Solution-Mediated, Solid-Solid Conversion," The Journal of Physical Chemistry, vol. 77, No. 19, 1973, 2313-2317. (Year: 1973).

U.S. Appl. No. 18/149,989, filed Jan. 4, 2023, Reynolds, Eric Charles.

U.S. Appl. No. 18/210,381, filed Jun. 15, 2023, Reynolds, Eric Charles.

U.S. Appl. No. 18/214,964, filed Jun. 27, 2023, Reynolds, Eric Charles.

"GC stellt Kasein-haltige Zahnschutzcreme vor—Vorbeugen statt reparieren", DZW Special IDS-Nachlese, 2005, English Abstract, 7 pages.

"MI Paste and MI Paste Plus", [retrieved on Oct. 21, 2014] from http://web.archive.org/web/20131223044114/http://www.gcamerica.com/products/preventive/MI_Paste, published on Dec. 23, 2013 as per Wayback Machine, 2 pages.

"Minimale Intervention fur Maximale Mundgesundheit", DZW Special, 2005, English Abstract, 1 page.

"Minimum Intervention: modernes Kariesmanagement—Weg vom chirurgischen, hin zum medizinischen Versorgungsansatz mit GC", IDS—31st International Dental Show, Cologne, Apr. 12-16, 2005 (Today—Independent Trade Show Daily—Saturday) English Abstract, 2 pages.

"Preventive Agents", The Dental Advisor, vol. No. 21, Issue No. 10, Dec. 2004, pp. 1-6.

"Products for the Dental Hygienist—Desensitizers", The Dental Advisor, vol. No. 23, Issue No. 6, Jul./Aug. 2006, 2 pages.

"Tooth Mousse—Pierre qui roule n'amasse pas mousse? Ben si!", Clinic, vol. No. 27, Apr. 2006, pp. 218-219 (English Abstract).

"Caseine phosphopeptide et phosphate de calcium amorphe: un complexe prometteur", Dialogue Dentaire, Printemps, 2005/W30, pp. 27-29, English Abstract provided.

"Editors' Choice Products—Prospec MI Paste", The Dental Advisor, vol. No. 22, Issue No. 5, Jun. 2005, 1 page.

"GC Tooth Mousse—Eine ganz andere Art der Prävention," Dental Spiegel, Feb. 2005, pp. 53-54.

"Putting mouths where the money is", DPRAsia, Jan./Feb. 2007, pp. 8-10.

"Tradition und modernes know how—ein Erfolgsrezept", Zahn Prax, vol. No. 8, Issue No. 5, 2005, p. 267.

Adamson, N. et al., "The analysis of multiple phosphoseryl-containing casein peptides using capillary zone electrophoresis", J. of Chromatography, vol. No. 646, Jun. 1993, pp. 391-396.

(56) References Cited

OTHER PUBLICATIONS

Adamson, N.J. et al., "Characterization of casein phosphopeptides prepared using alcalase: Determination of enzyme specificity", Enzyme and Microbial Tech., vol. No. 19, Aug. 1996, pp. 202-207.
Adamson, N.J. et al., "Characterization of Tryptic Casein Phosphopeptides Prepared Under Industrially Relevant Conditions", Biotec. and Bioeng., vol. No. 45, Issue No. 3, Feb. 1995, pp. 196-204.
Adamson, N.J. et al., "High performance capillary electrophoresis of casein phosphopeptides containing 2-5 phosphoseryl residues: Relationship between absolute electrophoretic mobility and peptide charge and size", Electrophoresis, vol. No. 16, 1995, pp. 525-528.
Adebayo, O.A. et al., "Effects of conditioners on microshear bond strength to enamel after carbamide peroxide bleaching and/or casein phosphopeptide-amorphous calcium phosphate (CPP-ACP) treatment", Journal of Dentistry, vol. No. 35, 2007, pp. 862-870.
Akinmade, A.O. et al., "Review Glass-Ionomer Cements as Adhesives, Part I, Fundamental Aspects and Their Clinical Relevance," Journal of Materials Science: Materials in Medicine, vol. No. 4, 1993, pp. 95-101.
Al-Zraikat, H. et al., "Development of glass ionomer cement incorporating casein phosphopeptide amorphous calcium phosphate (CPP-ACP) complex", Australian Dental Journal ADRF Special Research Supplement, vol. No. 52, Issue No. 4, 2007, p. S4.
Al-Zraikat, H. et al., "Incorporation of Casein-Phosphopeptide-Amorphous Calcium Phosphate into Glass Ionomer Cement", Abstract 0654, 84th General Session of the IADR, Jun. 28-Jul. 1, 2006, Brisbane, Australia, 1 page.
Allais, G., "Karies—Die Therapie", Journal of Continuing Dental Education, Jun. 2007, pp. 716-735.
Angmar, B. et al., "Studies on the Ultrastructure of Dental Enamel—IV. The Mineralization of Normal Human Enamel", J. Ultrastructure Research, vol. No. 8, 1963, pp. 12-23.
Aoba, T. et al., "Dental Fluorosis: Chemistry and Biology", Crit. Rev Oral Biol. Med., vol. No. 13, Issue No. 2, 2002, pp. 155-170.
Ardu, S. et al., "A minimally invasive treatment of severe dental fluorosis", Quintessence International, vol. No. 38, Issue No. 6, Jun. 2007, pp. 455-458.
Ardu, S. et al., "Minimally invasive treatment of white spot enamel lesions", Quintessence International, vol. No. 38, Issue No. 8, Sep. 2007, pp. 633-636.
Aytepe, Z. et al., "Effect of CCP-ACP on Oral Health of Cerebral Palsy Children", Abstract 3343, Jul. 2008, International Association for Dental Research, Toronto, Canada, 1 page.
Baig, A. et al., "HAP Dissolution Study II: SnF2 vs. NaF Dentifrice Study". 87th Session of the IADR (International & American Associations for Dental Research) Apr. 1-4, 2009 [online], [retrieved on Oct. 21, 2014]. Retrieved from internet, URL: dentalcare.com/media/en-US/research_ db/pdf/, p. 24.
Basting, RT et al., "The Effect of 10% Carbamide Peroxide Bleaching Material on Microhardness of Sound and Demineralized Enamel and Dentin In Situ" {Clinical Research} Operative Dentistry, vol. No. 26, 2001, pp. 531-539.
Bavetta, L.A. et al., "Protein Factors and Experimental Rat Caries", The Journal of Nutrition, vol. No. 63, 1957, pp. 107-117.
Benzian, H. et al., "Total and free available fluoride in toothpastes in Brunei, Cambodia, Laos, the Netherlands and Suriname", International Dental Journal, vol. No. 62, 2012, pp. 213-221.
Biesbrock, A.R. et al., "Reversal of Incipient and Radiographic Caries Through the Use of Sodium and Stannous Fluoride Dentifrices in a Clinical Trial," The Journal of Clinical Dentistry vol. No. IX, Issue No. 1, Feb. 1998, pp. 5-10.
Biesbrock, Aaron R. et al., "Dose response efficacy of sodium fluoride dentifrice at 9 and 21 months with supervised brushing", American Journal of Dentistry, vol. No. 16, Issue No. 5, Oct. 2003, 305-312.
Biesbrock, Aaron R., "Relative anti-caries efficacy of 1100, 1700, 2200, and 2800 ppm fluoride ion in a sodium fluoride dentifrice over 1 year", Community Dentistry and Oral Epidemiology, vol. No. 29, Jan. 2001, pp. 382-389.
Black, G.V. et al., "Mottled Teeth: An Endemic Developmental Imperfection of the Enamel of the Teeth Heretofore Unknown in the Literature of Dentistry", The Dental Cosmos, vol. No. LVIII, Issue No. 2., Feb. 1916, pp. 129-156.
Burwell, A.K. et al. "Dentifrice Protection Against Dentin Demineralization in an In Vitro Study", Abstract 1764, IADR, New Orleans, USA, Mar. 2007, 2 pages.
Burwell, A.K. et al., "Quantitative Tubule Occlusion in an In Vitro Remineralization/Demineralization Model", Abstract 0568, EADR 2006, Dublin, Ireland, Sep. 2006, 3 pages.
Cai, F. et al., "Effect of Addition of Citric Acid and Casein Phosphopeptide-Amorphous Calcium Phosphate to a Sugar-Free Chewing Gum on Enamel Remineralization in Situ", Caries Research, vol. No. 41, Feb. 2007, pp. 377-383.
Cai, F. et al., "Remineralization by Chewing Gum Containing CPP-ACP and Citric Acid", Abstract 190, 84th General Session of the IADR, Brisbane, Australia, Jun. 28, 2006-Jul. 1, 2006, pp. 240-243.
Cai, F. et al., "Remineralization of enamel subsurface lesions in situ by sugar-free lozenges containing casein phosphopeptide-amorphous calcium phosphate", Aus. Dent. J., vol. No. 48, Issue No. 4, 2003, pp. 240-243.
Calcium Glycerophosphate, DrugBank, pp. 1-5, XP002783472 (created Mar. 12, 2015) (retrieved Jul. 31, 2018).
Caplus, "NMR studies of a novel Calcium, phosphate and fluoride delivery vehicle <SYM97> S1-casein(59-79) by stabilized amorphous calcium fluoride phosphate nanocomplexes", Copyright 2005, 4 pages.
Carrillo, J. et al., "Nuevos avances tecnológicos en Odontologia Conservadora", La Gaceta Dental, vol. No. 193, Issue No. 213, Jun. 2008, pp. 218-219 (Spanish).
Chalmers, J. et al., "Minimal Intervention Dentistry in the New Millennium", Dentaltown, Feb. 2008, 2 pages.
Chalmers, J.M., "Minimal intervention dentistry: part 1. Strategies for Addressing the New Caries Challenge in Older Patients", JCDA, vol. No. 72, Issue No. 5, Jun. 2006, pp. 427-433.
Chelariu, C. et al., "Nuove prospettive nella prevenzione della carie Congresso Nazionale del Collegio dei Docenti di Odontoiatria Roma", Apr. 5-7, 2006, Poster session, published by "Doctor Os", No. 3, Mar. 2006, English Abstract, 1 page.
Chen, L. et al., "Calcium Release and Mechanical Properties of Experimental Calcium-Releasing Composites", Abstract 2572, IADR, New Orleans, USA, Mar. 2007, 1 page.
CIE Technical Committee, "Colorimetry—Second Edition", Publication CIE No. 15.2, 1986, 85 pages.
Cipolla, M. et al., "Fluoride and Calcium-Phosphate Effects on Fracture Toughness of Bleached Dentin", Abstract 1032, Toronto, Canada, Jul. 2008, 4 pages.
Coates, L., "Tooth mousse shows some unexpected beneficial side effects", Dental Asia, Nov./Dec. 2004, pp. 40-43.
Cochrane, N.J. et al., "QLF and TMR analysis of CPP-ACFP remineralized enamel in vitro", Abstract 192—84th General Session of the IADR, Brisbane, Australia Jun. 28, 2006-Jul. 1, 2006, 1 page.
Colgate, "Fluoride Conversions" colgateprofessional.com, Feb. 2013.
ColgatePalmolive, "Fluoride Conversions" dated Feb. 2013. www.colgateprofessional.com (2013).
Comar, L.P et al., "Effect of NaF, SnF2, andTiF4 Toothpastes on Bovine Enamel and Dentin Erosion-Abrasion In Vitro", International Journal of Dentistry, vol. No. 2012, Article ID 134350, pp. 1-6.
Crisp, S. et al., "Glass Ionomer Cements: Chemistry of Erosion", J. Dent. Res., vol. No. 55, Issue No. 6, 1976, pp. 1032-1041.
Cross, K.J. et al., "Casein Phosphopeptide-Amorphous Calcium Phosphate Nanocomplexes: A Model of the Casini Micelle Core", Centre for Oral Health Science, School of Dental Science, The University of Melbourne, 2008, pp. 1-42.
Cross, K.J. et al., "Casein Phosphopeptides in Oral Health—Chemistry and Clinical Applications", Current Pharmaceutical Design, vol. No. 13, Issue No. 8, 2007, pp. 793-800.
Cross, K.J. et al., "Cation-dependent structural features of beta-casein-(1-25)", Biochem. J., vol. No. 356, 2001, pp. 277-286.
Cross, K.J. et al., "NMR studies of a novel calcium, phosphate and fluoride delivery vehicle-alphaS1-casein(59-79) stabilized amor-

(56) References Cited

OTHER PUBLICATIONS phous calcium fluoride phosphate nanocomplexes", Biomaterials, vol. No. 25, 2004, pp. 5061-5069.
Cross, K.J. et al., "Physicochemical Characterization of Casein Phosphopeptide-Amorphous Calcium Phosphate Nanocomplexes", The Journal of Biological Chemistry, vol. No. 280, Issue No. 15, 2005, pp. 15362-15369.
Cross, K.J. et al., "Structural Studies of the b-Casein Phosphopeptide Bound to Amorphous Calcium Phosphate", J. Dent. Res., vol. No. 80, IADR Abstracts, Abstract 0490, 2001, p. 588.
Cross, K.J. et al., "Structure and 15N-Dynamics of Casein Phosphopeptide-Amorphous Calcium Phosphate Nanocomplexes", Abstract 2534, 84th General Session of the IADR, Jun. 28-Jul. 1, 2006, Brisbane, Australia, 1 page.
Cross, K.J. et al., "Ultrastructural Studies of the Casein Phosphopeptide-Amorphous Calcium Phosphate Nanoclusters", J. Dent. Res., vol. No. 80, IADR Abstracts, Abstract 0491, 2001, p. 588.
Cross, KJ et al., "Structural characterization of anticariogenic casein phosphopeptide alpha-s2 casein(46-70) complexed with amorphous calcium phosphate", Aust Dent J ADRF Special Research Supplement, vol. No. 52, Issue No. 4, 2007, pp. S10-S11.
Cross, KJ et al., "Structural Characterization of Beta-casein(1-25)-ACFP Complex", Aust Dent J ADRF Special Research Supplement, vol. No. 52, Issue No. 4, 2007, p. S12.
Curnow, M.M.T. et al., "A Randomised Controlled Trial of the Efficacy of Supervised Toothbrushing in High-Caries-Risk Children", Caries Research, vol. No. 36, 2002, pp. 294-300.
Database WPI Week 200316, Thomason Scientific, London, GB, 2003-165149, XP002537968 & SE 0 100 558 A, Mediteam Dental AB, Aug. 21, 2002, Abstract, 2 pages.
Davies, G.M. et al., "A randomized controlled trial of the effectiveness of providing free fluoride toothpaste from the age of 12 months on reducing caries in 5-6 year old children", Community Dental Health, vol. No. 19, 2002, pp. 131-136.
De Oliveira, A. et al., "In situ effect of a CPP-ACP chewing gum on enamel erosion associated or not with abrasion", Clin Oral Investig, vol. No. 21, Mar. 2016, pp. 339-346.
Deangelis, A.F. et al., "Molecular modelling of anticariogenic casein phosphopeptide aS2-CN(2-20) NMR spectroscopy derived constraints", Abstract 2997, 82nd General Session of the IADR, Mar. 2004, Honolulu, Hawaii, 1 page.
Denbesten, P.K. et al., "Biological Mechanisms of Fluorosis and Level and Timing of Systemic Exposure to Fluoride with Respect to Fluorosis", J Dent Res, vol. No. 71, Issue No. 5, May 1992, pp. 1238-1243.
Donovan, T., "Protocol for the prevention and management of root caries", Journal Compilation, vol. No. 20, Issue No. 6, 2008, pp. 405-411.
Duckworth, R.M. et al., "Effects of Mouthwashes of Variable NaF Concentration but Constant NaF Content on Oral Fluoride Retention", Caries Research, vol. No. 28, 1994, pp. 43-47.
Duckworth, R.M. et al., "Oral Fluoride Measurements for Estimation of the Anti-caries Efficacy of Fluoride Treatments", J Dent Res, vol. No. 71, Spec Iss, Apr. 1992, pp. 836-840.
Fahad, A.H. et al., "Effect of casein phosphopeptide-amorphous calcium phosphate on the microhardness and microscopic features of the sound enamel and initial caries-like lesion of permanent teeth, compared to fluoridated agents," Journal of Baghdad College Dentistry, vol. No. 24, Issue No. 4, 2012, pp. 114-120.
Farooq, I. et al., "A review of novel dental caries preventative material: Casein phosphopeptide-amorphous calcium phosphate (CPP-ACP) complex," King Saud University Journal of Dental Sciences, vol. No. 4, 2013, pp. 47-51.
Featherstone, J.D.B. et al., "An in situ Model for Simultaneous Assessment of Inhibition of Demineralization and Enhancement of Remineralization", J Dent Res, vol. No. 71, Spec. Iss., Apr. 1992, pp. 804-810.
Feinmann, J., "This won't hurt a bit," The Times, body&soul news, Mar. 12, 2005, pp. 4-5.
Fejerskov, O. et al., "The Effect of Fluoride on Tooth Mineralization", Fluoride in Dentistry—2nd edition, Chapter 8, Munksgaard, Copenhagen, 1996, pp. 112-152.
Fejerskov, O. et al., "Dental fluorosis—a handbook for health workers", Munksgaard, Copenhagen, 1988, pp. 32-77.
Fejerskov, O. et al., "Posteruptive changes in human dental fluorosis—a histological and ultrastructural study", Proc Finn Dent Soc, vol. No. 87, Issue No. 4, 1991, pp. 607-619.
Fejerskov, O. et al., "The Nature and Mechanisms of Dental Fluorosis in Man", J Dent Res, vol. No. 69, Spec Iss, Feb. 1990, pp. 692-700.
Ferrazzano, G.F. et al., "New Strategies in dental caries prevention: experimental study on casein phosphopetides", European Journal of Paedetric Dentistry, vol. No. 4, 2007, pp. 183-187.
Ferrazzano, G.F. et al., "Nuove strategie nella prevenzione della carie dentaria:studio sperimentale sui caseinofosfopeptidi", Prevenzione Odontostomatologica, vol. No. 4, 2005, pp. 15-21 Spanish.
Ferrazzano, G.F. et al., "Protective effect of yogurt extract on dental enamel demineralization in vitro", Australian Dental Journal, vol. No. 53, 2008, pp. 314-319.
Freml, L. et al., "Efficacy of Hypersensitivity Agents on Demineralization under Provisional Crowns", Abstract 1346, IADR Mar. 2007, New Orleans, USA, 2 pages.
Fuller, B.L. et al., "Efficacy of MI Paste in Preventing Demineralization in Overdenture Abutments", Abstract 0503, IADR Mar. 2007, New Orleans, USA, 2 pages.
Gagnaire, V. et al., "Phosphopeptides interacting with colloidal calcium phosphate isolated by tryptic hydrolysis of bovine casein micelles", Journal of Dairy Research, vol. No. 63, 1996, pp. 405-422.
Gandolfi, M.G. et al., "Calcium silicate coating derived from Portland cement as treatment for hypersensitive dentine", Journal of Dentistry, vol. No. 36, 2008, pp. 565-578.
GC America, Inc. "MI Paste™ and MI Paste Plus™ with Recaldent™ (CPP-ACP)", Inside Dentistry, vol. No 8, Issue No. 10, Oct. 2012 [online], [retrieved on Oct. 21, 2014]. Retrieved from internet, URL: www .dentalaegis.com/id/201 21 1 O/mi-paste-and-mi-paste-p I US-with-recaldent-cpp-acp>, 6 pages.
Giambro, N.J. et al., "Characterization of Fluorosed Human Enamel by Color Reflectance, Ultrastructure, and Elemental Composition", Caries Res., vol. No. 29, 1995, pp. 251-257.
Giniger, M. et al., "A 180-Day Clinical Investigation of the Tooth Whitening Efficacy of a Bleaching Gel with Added Amorphous Calcium Phosphate", J. of Clinical Dentistry. vol. No. 16, Issue No. 1, 2005, pp. 11-16.
Giniger, M. et al., "The clinical performance of professionally dispensed bleaching gel with added amorphous calcium phosphate", JADA, vol. No. 136, Mar. 2005, pp. 383-392.
Gisselsson, H., et al., "Effect of professional flossing with NaF or SnF2 gel on approximal caries in 13-16-year-old schoolchildren", Acta Odontologica Scandinavica, vol. No. 57, Issue No. 2, 1999, pp. 121-125.
Gugnani, S. et al., "Comparative evaluation of two commercially available desensitizing agents after scaling and root planing: an in vivo study", PERIO, vol. No. 5, Issue No. 2, 2008, pp. 121-129.
Haderlie, D.C. et al., "MI Paste and Fluoride effects on Secondary Caries", Abstract 0504, IADR Mar. 2007, New Orleans, USA, 2 pages.
Harper, D.S. et al., "Cariostatic Evaluation of Cheeses with Diverse Physical and Compositional Characteristics", Caries Res., vol. No. 20, 1986, pp. 123-130.
Harper, D.S. et al., "Modification of Food Cariogenicity in Rats by Mineral-Rich Concentrates from Milk", J. Dent Res., vol. No. 66, Issue No. 1, Jan. 1987, pp. 42-45.
Hartshorne, JE et al., "The relationship between plaque index scores, fluoride content of plaque, plaque pH, dental caries experience and fluoride concentration in drinking water in a group of primary school children", Journal of the Dental Association of South Africa, Vo. No. 49, Jan. 1994, pp. 5-10.
Hay, K.D. et al., "A Clinical Trial of the Anticaries Efficacy of Casein Derivatives Complexed with Calcium Phosphate in Patients

(56) References Cited

OTHER PUBLICATIONS with Salivary Gland Dysfunction", Oral. Surg. Oral Med Oral. Pathol Oral Radiol. Endod., vol. No. 93, Issue No. 3, Mar. 2002, pp. 271-275.
Haywood, V.B. et al., "History, safety, and effectiveness of current bleaching techniques and applications of the nightguard vital bleaching technique", Quintessence Int., vol. No. 23, Issue No. 7, Jul. 1992, pp. 471-488.
Hicks, J. et al., "Biological factors in dental caries: role of remineralization and fluoride in the dynamic process of demineralization and remineralization (part 3)", The Journal of Clinical Pediatric Dentistry, vol. No. 28, Issue No. 3, 2004, pp. 203-214.
Hicks, J. et al., "Casein Phosphopeptide-Amorphous Calcium Phosphate Paste: Root Surface Caries Formation", Abstract 3275, IADR, Baltimore, Maryland, Mar. 2005, 1 page.
Hidaka, S. et al., "A New Method for Study of the Formation and Transformation of Calcium Phosphate Precipitates: Effects of Several Chemical Agents and Chinese Folk Medicines", Archives of Oral Biol., vol. No. 36, Issue No. 1, 1991, pp. 49-54.
Holler, B.E. et al., "Fluoride uptake and distribution in enamel and dentin after application of different fluoride solutions", Clin Oral Invest, vol. No. 6, 2002, pp. 137-144.
Holloway, P.J. et al., "Effects of Various Sucrose: Casein Ratios in Purified Diets on the Teeth and Supporting Structures of Rats", Arch. Oral Biol., vol. No. 3, 1961, pp. 185-200.
Holt, C. et al., "Ability of a b-casein phosphopeptide to modulate the precipitation of calcium phosphate by forming amorphous dicalcium phosphate nanoclusters", Biochem J., vol. No. 314, 1996, pp. 1035-1039.
Holt, C., "An equilibrium thermodynamic model of the sequestration of calcium phosphate by casein micelles and its application to the calculation of the partition of salts in milk", European Biophysics Journal, 2004, pp. 421-434.
Huang, A. et al., "Remineralization of Eroded Teeth Using CPP-ACP Paste", Abstract 3267, International Association for Dental Research, Toronto, Canada, Jul. 2008, 1 page.
Huq, N.L. et al., "Nascent Helix in the Multiphosphorylated Peptide as2-Casein(2-20)", Journal of Peptide Science, vol. No. 9, 2003, pp. 386-392.
Huq, N.L. et al., "A 1H-NMR study of the casein phosphopeptide as1-casein (59-79)", Biochimica et Biophysica Acta, vol. No. 1247, 1995, pp. 201-208.
Huq, N.L. et al., "Molecular Modeling of a Multiphosphorylated Sequence Motif Bound to Hydroxyapatite Surfaces", J. Mol. Model., vol. No. 6, 2000, pp. 35-47.
Huq, N.L. et al., "Molecular modelling of the multiphosphorylated casein phosphopeptide aS1-casein(59-79) based on NMR constraints", J. Dairy Res., vol. No. 71, 2004, pp. 28-32.
Iijima, Y. et al., "Acid Resistance of Enamel Subsurface Lesions Remineralized by a Sugar-Free Chewing Gum Containing Casein Phosphopeptide-Amorphous Calcium Phosphate", Caries Res., vol. No. 38, 2004, pp. 551-556.
Iijima, Y. et al., "Acid Resistance of Remineralized Enamel by a Sugar-Free Chewing Gum", Abstract 0184, 84th General Session of the IADR, Jun. 28-Jul. 1, 2006, Brisbane, Australia, 1 page.
Imfeld, T., "Prevention of progression of dental erosion by professional and individual prophylactic measures," Eur J Oral Sci, vol. No. 104, 1996, pp. 215-220.
Inaba, D. et al. "Intraoral changes in NaOCI-treated Root Dentin Lesions: A Pilot Study.", J. Dental Health, vol. No. 50, 2000, pp. 824-826, Abstract.
Inaba, D. et al., "Effect of Sodium Hypochlorite Treatment on Remineralization of Human Root Dentine in vitro", Caries Research, vol. No. 30, 1996, pp. 218-224.
Kandelman, D. et al., "A 24-month Clinical Study of the Incidence and Progression of Dental Caries in Relation to Consumption of Chewing Gum Containing Xylitol in School Preventive Programs", J Dent Res, vol. No. 69, Issue No. 11, Nov. 1990, pp. 1771-1775.
Kariya, S. et al., "Fluoride Effect on Acid Resistance Capacity of CPP-ACP Containing Material", Abstract 2045, 82nd General Session of the IADR, Mar. 2004, Honolulu, Hawaii, 1 page.
Kariya, S. et al., "Remineralization of Enamel Lesion by a Novel Cream with both CPP-ACP and Fluoride", Poster Session 136, 54th Annual ORCA Congress, 2007, 1 page.
Keçik, D. et al., "Effect of Acidulated Phosphate Fluoride and Casein Phosphopeptide-Amorphous Calcium Phosphate Application on Shear Bond Strength of Orthodontic Brackets", Angle Orthodontist, vol. No. 78, Issue No. 1, 2008, pp. 129-133.
Khan, S., "White Spots on Teeth", Buzzle.com, https://www.buzzle.com/articles/white-spots-on- teeth.html, published Jan. 8, 2010, 2 pages.
Kilian, M. et al., "The oral microbiome—an update for oral healthcare professionals", British Dental Journal, vol. No. 221, Issue No. 10, Nov. 18, 2016, pp. 657-666.
Kim, K.-B. et al., "Remineralization of the artificial caries lesion using CPP-ACP and fluoride", Abstract 3280, International Association for Dental Research, Toronto, Canada, Jul. 2008, 1 page.
Kowalczyk, A. et al., "Evaluation of the product based on Recaldent™ technology in the treatment of dentin hypersensitivity", Advances in Medical Sciences, vol. No. 51, Suppl. 1, 2006, pp. 40-42.
Krobicka, A. et al., "The Effects of Cheese Snacks on Caries in Desalivated Rats", J. Dent Res., vol. No. 66, Issue No. 6, Jun. 1987, pp. 1116-1119.
Kumar, VLN et al., "The effect of casein phosphopeptide-amorphous calcium phosphate on remineralization of artificial caries-like lesions: an in vitro study", Australian Dental Journal, vol. No. 53, 2008, pp. 34-40.
Lasfargues, J. et al., "La Remineralisation Des Lesions Carieuses (2) Synergies Therapautiques", Realites Cliniques, vol. No. 15, Issue No. 3, 2004, pp. 261-275, English Abstract.
Legeros, R.Z., "Calcium Phosphates in Demineralization/Remineralization Processes", J Clinical Dent, vol. No. 10, Issue No. 2, 1999, pp. 65-73.
Lewis, J., "Brush, floss and mousse?", Women Dentistry Journal, Winter 2005, vol. No. 2, Issue No. 4, pp. 18-19.
Little, E. et al., "An equilibrium thermodynamic model of the sequestration of calcium phosphate by casein phosphopeptides", European Biophysics Journal, vol. No. 33, 2004, pp. 435-447.
Loesche, W.J., "Role of Streptococcus mutans in Human Dental Decay", Microbial. Rev., vol. No. 50, Issue No. 4, Dec. 1986, pp. 353-380.
Lynch, R.J.M. et al., "Low-Levels of fluoride in plaque and saliva and their effects on the demineralisation and remineralisation of enamel; role of fluoride toothpastes", International Dental Journal, vol. No. 54, Issue No. 5, pp. 304-309.
Madhavan, S et al., "Dentinal hypersensitivity: A comparative clinical evaluation of CPP-ACPF, sodium fluoride, propolis, and placebo", Journal of Conservative Dentistry, 2012; 15(4): 315-318.
Malcmacher, L., "Enamel Remineralization: The Medical Model of Practicing Dentistry", Dentistry Today, Nov. 2006, 2 pages.
Malcmacher, L., "Vitamins for teeth", Common Sense Dentistry, www.dentaleconomics.com, Oct. 2006, pp. 130 and 144.
Manton, D.J. "Dental Caries: Where to From Here?", Ann Roy Australas Coll Dent Surg, vol. No. 19, 2008, pp. 73-76.
Manton, D.J. et al., "In Situ Remineralisation by Sugar-Free Gums, One Containing CPP-ACP", Abstract 0020, 45th Annual Meeting of Australian/New Zealand Division of the IADR, Sep. 2005, 1 page.
Manton, D.J. et al., "Remineralization of enamel subsurface lesions in situ by the use of three commercially available sugar-free gums", International Journal of Paediatric Dentistry, vol. No. 18, 2008, pp. 284-290.
Manton, D.J. et al., "Remineralization of White Spot Lesions in situ by Tooth Mousse", Abstract 0185, 84th General Session of the IADR, Jun. 28-Jul. 1, 2006, Brisbane, Australia, 1 page.
Manton, D.J., "Promoting Remineralization: Using Casein Phosphopeptide-Stabilized Amorphous Calcium (Fluoride) Phosphate. A Chemical Approach", EAPD, Amsterdam, Jun. 8-11, 2006, 1 page.
Manton, DJ et al., "Effect of ozone and Tooth Mousse™ on the efficacy of peroxide bleaching", Australian Dental Journal, vol. No. 53, 2008, pp. 128-132.

(56) References Cited

OTHER PUBLICATIONS

Martinez-Pablon, M. et al., "Comparison of the Effect of Two Sugar-Substituted Chewing Gums on Different Caries- and Gingivitis-Related Variables: A Double-Blind, Randomized, Controlled Clinical Trial", Clinical Oral Investigations, vol. No. 18, 2014, pp. 589-598.
Mazzaoui, S.A. et al., "Incorporation of Casein Phosphopeptide-Amorphous Calcium Phosphate into a Glass-ionomer Cement", Journal of Dental Research, vol. No. 82, Issue No. 11, 2003, pp. 914-918.
Melkers, M.J., "Keeping Focused on the Finish Line . . . Accomplishing Goals with Traditional and Progressive Technologies", Dentaltown, vol. No. 5, Issue No. 11, Nov. 2004, pp. 60, 62, 64 & 66.
Mellberg, J.R. et al., "Effect of soluble calcium on fluoride uptake by enamel from sodium monofluorophosphate", J Dent Res., vol. No. 61, Issue No. 12, Dec. 1982, pp. 1394-1396.
MI Paste™ and MI Paste Plus™ [retrieved on Feb. 16, 2015] Retrieved from internet , URL: http://web.archive.org/web/20140701070616/http://www.mipaste.com/about.php> published on Dec. 4, 2013 as per Wayback Machine whole document Wayback machine used to determine publication date, 2 pages.
Mickenautsch, S., "An Introduction to Minimal Intervention Dentistry (MI)", Dental News, vol. No. XIV, Issue No. IV, 2007, pp. 13-20.
Milnar, F.J., "Considering Biomodification and Remineralization Techniques as Adjuncts to Vital Tooth-Bleaching Regimens", Compendium, vol. No. 28, Issue No. 5, May 2007, pp. 234-240.
Minami, K. et al., "Effects of Cheese and Milk Containing CPP-ACP on Enamel Remineralization", 2049—82nd General Session of the IADR, Mar. 2004, Honolulu, Hawaii, 1 page.
Mintel, "Mineralising Toothpaste," from Database GNPD, Database Accession No. 1368327, Aug. 2010, 3 pages.
Misra, S. et al., "Early Childhood Caries—A Review", Dental Update, vol. No. 34, Dec. 2007, pp. 556-564.
Mitthra, S. et al., "Mineral Loss before and after Bleaching and Mineral Uptake on Application of Remineralizing Agent", Indian Journal of Multidisciplinary Dentistry and Endodontics, vol. No 1, Issue No. 1, Jan. 2010, 4 pages.
Miyazaki, M. et al., "Using Ultrasound Transmission Velocity to Analyze Demineralization of Tooth Substrate", Abstract 94, 52nd ORCA Congress, Jul. 2005, Indianapolis, USA, Caries Res, vol. No. 39, p. 319.
Morgan, M.V. et al. "A Clinical Trial Measuring White Spot Lesion Progression and Regression", Abstract 0112, Jul. 2008, Toronto, Canada, 1 page.
Morgan, M.V. et al., "CPP-ACP gum slows progression and enhances regression of dental caries", Abstract 2445, 84th General Session of the IADR, Jun. 28-Jul. 1, 2006, Brisbane, Australia, 1 page.
Morgan, M.V. et al., "The Anticariogenic Effect of Sugar-Free Gum Containing CPP-ACP Nanocomplexes on Approximal Caries Determined Using Digital Bitewing Radiography", Caries Research, vol. No. 42, 2008, pp. 171-184.
Morgan, MV et al., "Clinical Trial of Tooth Mousse on White Spot Lesions", Cooperative Research Centre for Oral Health Science, Briefing Paper No. 2, Jul. 2008, 4 pages.
Moule, C.A. et al., "Resin bonding using an all-etch or self-etch adhesive to enamel after carbamide peroxide and/or CPP-ACP treatment", Australian Dental Journal, vol. No. 52, Issue No. 2, 2007, pp. 133-137.
Mount, GJ, "A new paradigm for operative dentistry", Australian Dental Journal, vol. No. 52, Issue No. 4, 2007, pp. 264-270.
Munjal, D. et al., "Assessment of White Spot Lesions and In-Vivo Evaluation of the Effect of CPP-ACP on White Spot Lesions in Permanent Molars of Children", Journal of Clinical and Diagnostic Research, vol. No. 10, Issue No. 5, May 2016, pp. 149-154.
Murata, Y. et al., "Remineralization Power by Xylitol Chewing Gums", Abstract 2046, 82nd General Session of the IADR, 2004, Honolulu, Hawaii, 1 page.
Narayana, T. et al., "An in vitro study of wear prevention in dentine", Abstract 2424, 84th General Session of the IADR, Jun. 28-Jul. 1, 2006, Brisbane, Australia, 1 page.
Ng, F. et al., "Aesthetic management of severely fluorosed incisors in an adolescent female", Australian Dental Journal, vol. No. 52, Issue No. 3, 2007, pp. 243-248.
O'Hehir, T., "Caries- More Than a Filling", Hygientown.com, Jul./Aug. 2008, pp. 8-12.
Ono, T. et al., "Complexes of Casein Phosphopeptide and Calcium Phosphate Prepared from Casein Micelles by Tryptic Digestion", Biosci. Biotech. Biochem., vol. No. 58, Issue No. 8, 1994, pp. 1376-1380.
Ono, T. et al., "Preparation of Casein Phosphopeptides from Casein Micelles by Ultrafiltration", Biosci. Biotech. Biochem., vol. No. 59, Issue No. 3, 1995, pp. 510-511.
Oshiro, M. et al., "Effect of CPP-ACP paste on tooth mineralization: an FE-SEM study", Journal of Oral Science, vol. No. 49, Issue No. 2, 2007, pp. 115-120.
P.J. Eke, et al. "Prevalence of Periodontitis in Adults in the United States: 2009 and 2010." J Dent Res 91:914-920 (2012). (Year: 2012).
Pelletier, P. et al., "Study of the Hyrolyisis Reaction of the P03F2 Anion in Aqueous Solution", Z. Anorg. Alig. Chem., 1990, vol. No. 581, pp. 190-198.
Perdigao, J. et al., "Contemporary Trends and Techniques in Tooth Whitening: A Review", Practical Procedures & Aesthetic Dentistry, vol. No. 16, Issue No. 3, 2004, pp. 185-192.
Perich, J.W. et al., "Efficient Solution-Phase Synthesis of Multiple O-Phosphoseryl-Containing Peptides Related to Casein and Statherin", Int. J. Pept. Protein Res., vol. No. 40, 1992, pp. 81-88.
Perich, J.W. et al., "The Use of Synthetic Phosphopeptides for Epitope Mapping of the aS1-Casein Phosphopeptide Segment 59-70", Bioorg. Med. Chem. Lett., vol. No. 2, 1992, pp. 1153-1154.
Peschke, J.C. et al., "Nucleating Ability of Calcium Phosphate-Protein-Composites", Abstract 2244, IADR, Mar. 2007, New Orleans, USA, 2 pages.
Piekarz, C. et al., "An in vitro assessment of the role of Tooth Mousse in preventing wine erosion", Australian Dental Journal, vol. No. 53, 2008, pp. 22-25.
Pietrzycka, K. et al., "Chemical methods of treatment of dental caries: the action and application of CPP-ACP", Kwartalnik Stomatologa Praktyka Polish & English Journal for Dentists, E-Dentico, vol. No. 2, Issue No. 18, 2008, pp. 68-74.
Pitts, N.B., "Are We Ready to Move from Operative to Non-Operative/Preventive Treatment of Dental Caries in Clinical Practice? ", Caries Res, vol. No. 38, 2004, pp. 294-304.
Plate, U. et al., "Investigation of the early mineralisation on collagen in dentine of rat incisors by quantitative electron spectroscopic diffraction (ESD)", Cell Tissue Res, vol. No. 278, 1994, pp. 543-547.
Poitevin, A. et al., "Clinical Effectiveness of a CPP-ACP Creme for Tooth Hypersensitivity Treatment", EADR Istanbul, Aug. 24-28, 2004, Abstract 0136, 1 page.
Quartarone, E. et al., "Surface kinetic roughening caused by dental erosion: an atomic force microscopy study", Journal of Applied Physics, vol. No. 103, 2008, 104702, 6 pages.
Rahiotis, C. et al., "Characterization of oral films formed in the presence of a CPP-ACP agent: An in situ study", Journal of Dentistry, vol. No. 36, 2008, pp. 272-280.
Rahiotis, C. et al., "Effect of a CPP-ACP agent on the demineralization and remineralization of dentine in vitro", Journal of Dentistry, vol. No. 35, 2007, pp. 695-698.
Ramadas, Y., "The oral care for children with malignancies", Synopses: The Newsletter of the Australian and New Zealand Society of Paediatric Dentistry, Issue No. 28, Mar. 2004, pp. 1-20.
Ramalingam, L. et al., "Adding Caesin Phosphopetide-amorphous Calcium Phosphate to Sports Drinks to Eliminate In Vitro Erosion", Pediatric Dentistry, vol. No. 27, Issue No. 1, 2005, pp. 61-67.
Ramalingam, L. et al., "An in Vitro Investigation of the Effects of Casein Phosphopeptide-Stabilized Amorphous Calcium Phosphate (CPP-ACP) on Erosion of Human Dental Enamel by a Sports Drink", J Dent Res., vol. No. 81, Spec Iss A, 2002, Abstract 2810, p. A-351.

(56) References Cited

OTHER PUBLICATIONS

Ramalingam, L. et al., "Erosion of Human Dental Enamel by Sports Drinks", Synopses, vol. No. 27, 2003, pp. 16-19.
Ranjitkar, S. et al., "Enamel wear prevention under conditions simulating bruxism and acid regurgitation", Abstract 2428, 84th General Session of the IADR, Jun. 28-Jul. 1, 2006, Brisbane, Australia, 1 page.
Ranjitkar, S. et al., "The Role of Tooth Mousse in preventing enamel wear," Poster 0375, Session 39, 42nd Annual Meeting of IADR, Continental European and Israeli Divisions, Sep. 26-29, 2007, 1 page.
Ranjitkar, S. et al., "The Role of Tooth Mousse in Reducing Erosive Tooth Wear", Abstract 2500, International Association for Dental Research, Jul. 2008, Toronto, Canada, 1 page.
Rees, J. et al., "Pronamel and tooth mousse: An initial assessment of erosion prevention in vitro", Journal of Dentistry, vol. No. 35, 2007, pp. 355-357.
Reeves, R. et al., "Calcium Phosphate Sequestering Phosphopeptide from Casein", Science, vol. No. 128, 1958, p. 472.
Reich, E., "Das kleine gewisse Etwas zur Remineralisation", Zahnmedizin, vol. No. 95, Issue No. 21, 2005, pp. 2-9, English Abstract.
Reich, E., "Die Betreuung von Kariespatienten in der Praxis", Quintessenz, vol. No. 59, Issue No. 12, 2008, pp. 1301-1307, English Abstract.
Reich, E., "Flüssiger Zahnschmelz", Dental Magazine, 2005, English Abstract, 4 pages.
Reich, E., "GC Tooth Mousse—Ein neuer Ansatz zur Remineralisation", Kongress: Wissenschaft und Praxis der Sanften Zahnheilkunde, Lindau am Bodensee, Mar. 3-4, 2006, English Abstract, 4 pages.
Reich, E., Dental Products Report Europe, Jan. 1, 2006, 9 pages.
Retention in Plaque and Remineralization of Enamel Lesions by Various Forms of Calcium in a Mouthrinse or Sugar-Free Chewing Gum, School of Dental Science, The University of Melbourne pp. 1-24.
Reynolds, E., "The Role of Phosphopeptides in Caries Prevention", Dental Perspectives, Edition 3, Nov. 1999, pp. 6-7.
Reynolds, E.C. et al., "Confectionary Composition and Rat Caries", Caries Res., vol. No. 21, 1987, pp. 538-545.
Reynolds, E.C. et al., "Effect of Adsorbed Protein on Hydroxyapatite Zeta Potential and Streptococcus mutans Adherence", Infection and Immunity, vol. No. 39, Issue No. 3, Mar. 1983, pp. 1285-1290.
Reynolds, E.C. et al., "Effect of Casein and Whey-Protein Solutions on Caries Experience and Feeding Patterns of the Rat", Archs. oral. Biol., vol. No. 29, Issue No. 11, 1984, pp. 927-933.
Reynolds, E.C. et al., "Enamel Remineralization by Chewing Gum Containing Casein Phosphopeptide-Amorphous Calcium Phosphate", J Dent Res, vol. No. 80, IADR Abstracts, Abstract 0489, 2001, p. 588.
Reynolds, E.C. et al., "Phosphoprotein Inhibition of Hydroxyapatite Dissolution", Calcif. Tissue Int., vol. No. 34, 1982, pp. S52-S56.
Reynolds, E.C. et al., "Protein Dissimilation by Human Salivary-sediment Bacteria", J. Dent.Res., vol. No. 68, Issue No. 1, Feb. 1989, pp. 124-129.
Reynolds, E.C. et al., "Reduction of Chocolate's Cariogenicity by Supplementation with Sodium Caseinate", Caries Res., vol. No. 21, 1987, pp. 445-451.
Reynolds, E.C. et al., "Retention in Plaque and Remineralization of Enamel Lesions by Various Forms of Calcium in a Mouthrinse or Sugar-free Chewing Gum", J Dent Res, vol. No. 82, Issue No. 3, 2003, pp. 206-211.
Reynolds, E.C. et al., "A Review of the Effect of Milk on Dental Caries", Aust. J. Dairy Tech., vol. No. 34, Dec. 1979, pp. 175-179.
Reynolds, E.C. et al., "A Selective Precipitation Purification Procedure for Multiple Phosphoseryl-Containing Peptides and Methods for Their Identification", Anal. Biochem., vol. No. 217, Issue No. 2, 1994, pp. 277-284.
Reynolds, E.C. et al., "Additional Aids to the Reminersalisation of Tooth Structure," Preservation and Restoration of Tooth Structure, Chapter 8, 2005, pp. 111-118.
Reynolds, E.C. et al., "Advances in Enamel Remineralization: Casein Phosphopeptide-Amorphous Calcium Phosphate", J. Clin. Dent., vol. No. X, Issue No. 2, 1999, pp. 86-88.
Reynolds, E.C. et al., "Anticariogenicity of Calcium Phosphate Complexes of Tryptic Casein Phosphopeptides in the Rat", J Dent Res, vol. No. 74, Issue No. 6, 1995, pp. 1272-1279.
Reynolds, E.C. et al., "Cariogenicity of a Confection Supplemented with Sodium Caseinate at a Palatable Level", Caries. Res., vol. No. 23., 1989, pp. 368-370.
Reynolds, E.C. et al., "Effect of Milk on Caries Incidence and Bacterial Composition of Dental Plaque in the Rat", Archs oral Biol., vol. No. 26, Issue No. 5, 1981, pp. 445-451.
Reynolds, E.C. et al., "Fluoride and Casein Phosphopeptide-Amorphous Calcium Phosphate", J Dent Res, vol. No. 87, Issue No. 4, 2008, pp. 344-348.
Reynolds, E.C. et al., "Improved Plaque Uptake and Enamel Remineralization by Fluoride with CPP-ACP", Abstract 2538, 84th General Session of the IADR, Jun. 28-Jul. 1, 2006, Brisbane, Australia, 1 page.
Reynolds, E.C., "The Prevention of Sub-surface Demineralization of Bovine Enamel and Change in Plaque Composition by Casein in an Intra-oral model", J. Dental Res., vol. No. 66, Issue No. 6, 1987, pp. 1120-1127.
Reynolds, E.C., "Anticariogenic Casein Phosphopeptides", Prot. Peptide Lett., vol. No. 6, Issue No. 5, 1999, pp. 295-303.
Reynolds, E.C., "Anticariogenic complexes of amorphous calcium phosphate stabilized by casein phosphopeptides: A review", Journal of Special Care in Dentistry, vol. No. 18, Issue No. 1, Jan./Feb. 1998, pp. 8-16.
Reynolds, E.C., "Calcium phosphate-based remineralizatron systems: scientific evidence?", Australian Dental Journal, vol. No. 53, 2008, pp. 268-273.
Reynolds, E.C., "Caries Prevention and Oral Health", Health Aspects of Dairy Products/Caries Prevention and Oral Health, 2002, pp. 1306-1313.
Reynolds, E.C., "Dairy Components in Oral Health", Aust. J. Dairy Tech., vol. No. 58, Issue No. 2, Aug. 2003, pp. 79-81.
Reynolds, E.C., "Dairy Products and Dental Health," Proceedings of the Nutrition Society of Australia, 1995, pp. 95-102.
Reynolds, E.C., "Remineralization of Enamel Subsurface Lesions by Casein Phosphopeptide-stabilized Calcium Phosphate Solutions", J Dent Res., vol. No. 76, Issue No. 9, Sep. 1997, pp. 1587-1595.
Reynolds, EC., "Remineralization of early enamel caries by anticariogenic casein phosphopeptide-amorphous calcium phosphate nanocomplexes", Dental Practice, Nov./Dec. 2001, 3 pages.
Roberts, A.J., "Role of Models in Assessing New Agents for Caries Prevention-Non-Fluoride Systems", Adv. Dent. Res., vol. No. 9, Issue No. 3, Nov. 1995, pp. 304-311.
Roberts, MJ et al., "Remineralisation of fluorotic enamel lesions by casein phosphopeptide-amorphous calcium fluorophosphate (CPP-ACFP) solution", IADR, ANZ Division, Abstract 54, 2000, 2 pages.
Robinson, C. et al., "Effect of Surface Zone Deproteinisation on the Access of Mineral lons into Subsurface Carious Lesions of Human Enamel", Caries Res, vol. No. 24, 1990, pp. 226-230.
Rose, R.K., "Binding Characteristics of Streptococcus Mutans for Calcium and Casein Phosphopeptide", Caries. Res., vol. No. 34, 2000, pp. 427-431.
Rose, R.K., "Effects of an Anticariogenic Casein Phosphopeptide on Calcium Diffusion in Streptococcal Model Dental Plaques", Archives of Oral Biology, vol. No. 45, 2000, pp. 569-575.
Rosen, S. et al., "Effect of Cheese, With and Without Sucrose, On Dental Caries and Recovery of Streptococcus mutans in Rats", J. Dent. Res., vol. No. 63, Issue No. 6, Jun. 1984, pp. 894-896.
Rozwadowska, E., "Children and private dentistry", Private Dentistry, May 2006, pp. 109-113.
Sakaguchi, Y. et al. "Remineralization Potential of CPP-ACP and its Synergy with Fluoride", Abstract 0191, 84th General Session of the IADR, Jun. 28-Jul. 1, 2006, Brisbane, Australia, 3 pages.
Sakaguchi, Y. et al., "Preventing Acid Induced Enamel Demineralization Using CPP-ACP Containing Paste", Abstract 2055, IADR, Mar. 2005, Baltimore, Maryland, USA, 1 page.

(56) References Cited

OTHER PUBLICATIONS

Sakr, A.M. et al., "The Effect of Recaldent (CPP-ACP) on the most putative bacteria in caries and chronic gingivitis", Ain Shams Dental Journal, vol. No. X, Issue No. 2, Jun. 2007, pp. 211-219.
Sato, T. et al., "Caries Prevention Potential of a Tooth-coating Material Containing Casein Phosphopeptide-Amorphous Calcium Phosphate (CPP-ACP)," IADR, General Session, Goteborg, 2003, Abstract 1007, 3 pages.
Schüpbach, P. et al., "Incorporation of Caseinoglycomacropeptide and Caseinophosphopeptide into the Salivary Pellicle Inhibits Adherence of Mutans Streptococci", J. Dent. Res, vol. No. 75, Issue No. 10, Oct. 1996, pp. 1779-1788.
Schweigert, B.S. et al., "Dental Caries in the Cotton Rat—VI. The Effect of the Amount of Protein, Fat and Carbohydrate in the Diet on the Incidence and Extent of Carious Lesions", J. Nutr., vol. No. 31, 1946, pp. 439-447.
Shaw, J.H., "Effects of dietary composition on tooth decay in the albino rat", J. Nutr., vol. No. 41, 1950, pp. 13-23.
Sheharyar, S. et al., "Efficacy of MI Paste for Sensitivity Associated With Vital Bleaching", Abstract 2041, IADR, Mar. 2007, New Orleans, USA, 2 pages.
Shen, P. et al., "Enamel remineralization by a mouthrinse containing casein phosphopeptide-amorphous calcium phosphate and fluoride in an in situ model", Australian Dental Journal ADRF Special Research Supplement, vol. No. 49, Issue No. 4, 2004, p. S19.
Shen, P. et al., "Remineralization of Enamel Subsurface Lesions by Sugar-free Chewing Gum Containing Casein Phosphopeptide-Amorphous Calcium Phosphate", J Dent Res, vol. No. 80, Issue No. 12, 2001, pp. 2066-2070.
Shen, P. et at., "Remineralization by a Mouthrinse Containing CPP-ACP at pH 5.5", Abstract 0189, 84th General Session of the IADR, Jun. 28-Jul. 1, 2006, Brisbane, Australia, 1 page.
Silva, M. et al., "Fluoride content of infant formulae in Australia", Australian Dental Journal, vol. No. 41, Issue No. 1, 1996, pp. 37-42.
Silva, M.F. de A. et al., "Effects of Water-soluble Components of Cheese on Experimental Caries in Humans", J Dent Res, vol. No. 66, Issue No. 1, Jan. 1987, pp. 38-41.
Sim, C. et al., "Anti-caries effect of CPP-ACP in irradiated nasopharyngeal carcinoma patients", Clinical Oral Investigations, vol. No. 19, Issue No. 5, 2015, pp. 1005-1011.
Skold-Larsson, K. et al., "Fluoride concentration in plaque in adolescents after topical application of different fluoride varnishes", Clin Oral Invest., vol. No. 4, 2000, pp. 31-34.
Slomiany, B.L. et al., "Salivary Mucins in Oral Mucosal Defense", Gen. Pharmac., vol. No. 27, Issue No. 5, 1996, pp. 761-771.
Smith, S. et al., "Ultramorphological evaluation of dentin after treatment with different desensitizing agents", Abstract 0941, IADR, 2007, New Orleans, USA, 2 pages.
Smolenski, D. et al., "MI Paste and Fluoride for Caries Prevention In-Vitro", Abstract 0505, IADR, 2007, New Orleans, USA, 2 pages.
Steinberg, S., "A Modern Paradigm for Caries Management, Part 1: Diagnosis and Treatment", Dentistry Today, Feb. 2007, 11 pages.
Steinberg, S., "A Modern Paradigm for Caries Management, Part 2: A Practical Protocol", Dentistry Today, Jun. 2007, 6 pages.
Stößer, L., et al., "Kariesprotektive Eigenschaften des durch Caseinphosphopeptid stabilisierten amorphen Calciumphosphat-Nanokomplexes (CPP-ACP)", Deutsche Zahniirztliche Zeitschrift, vol. No. 62, Issue No. 9, 2008, pp. 579-588 (English Abstract).
Sudjalim, T.R. et al., "Prevention of demineralization around orthodontic brackets in vitro", American Journal of Orthodontics and Dentofacial Orthopedics., 2007, vol. No. 131, Issue No. 6, pp. 705.e1-705.e9.
Sudjalim, T.R. et al., "Prevention of white spot lesions in orthodontic practice: a contemporary review", Australian Dental Journal, vol. No. 51, Issue No. 4, 2006, pp. 284-289.
Sukasaem, H. et al., "Effect of CPP-ACP on Hardness of Enamel Eroded by Cola-drink", Abstract 1673, 84th General Session of the IADR, Jun. 28-Jul. 1, 2006, Brisbane, Australia, 1 page.
Takamizawa, T. et al., "Determination of Demineralization of Tooth Substrate by Use of an Ultrasonic Device", Japan J Conserv Dent, Jun. 47, Spring Issue 24, Abstract B-4, 2004, 2 pages.
Talbo, G.H. et al., "MALDI-PSD-MS Analysis of the Phosphorylation Sites of Caseinomacropeptide", Peptides, vol. No. 22, 2001, pp. 1093-1098.
Tantbirojn, D. et al., "Changes in surface hardness of enamel by a cola drink and a CPP-ACP paste", Journal of Dentistry, vol. No. 36, 2008, pp. 74-79.
Tay, L.Y. et al. "Assessing the Effect of a Desensitizing Agent Used Before In-office Tooth Bleaching," The Journal of the American Dental Association, vol. No. 140, Issue No. 10, Oct. 2009, pp. 1245-1251.
Ten Cate, J.M., "Current concepts on the theories of the mechanism of action of fluoride", Acta Odontol Scand, vol. No. 57, 1999, pp. 325-329.
Theerapiboon, U. et al., "Remineralization of Artificial Caries by CPP-ACP Paste", Abstract 3274, Jul. 2008, International Association for Dental Research, Toronto, Canada, 1 page.
Trajtenberg, C.P. et al., "CPP-ACP Paste with Fluoride: In Vitro Root Surface Caries Formation", Abstract 0500, IADR, 2007 New Orleans, USA, 2 pages.
Translation of Japanese Office Action from Application No. 2002-590925, Nov. 18, 2018.
Translation of Russian Office Action from Application No. 2007123603, May 26, 2009, 3 pages.
Turssi, C.P. et al., "Progression of erosion following use of calcium and phosphorus compounds", Abstract 2499, Jul. 2008, International Association for Dental Research, Toronto, Canada, 1 page.
Ung, M. et al. "Investigation of the binding of casein phosphopeptides to the major enamel pellicle proteins", Australian Dental Journal ADRF Special Research Supplement, vol. 49, Issue No. 4, 2004, pp. S19-S20.
Vegarud et al "Mineral-binding milk proteins and peptides; occurrence, biochemical and technological characteristics", British Journal of Nutrition (2000), vol. 84, Suppl. 1, p. S91-S98. (Year: 2000).
Vlacic, J. et al., "Combined CPP-ACP and photoactivated disinfection (PAD) therapy in arresting root surface caries: a case report", British Dental Journal, vol. No. 203, Issue No. 8, Oct. 27, 2007, pp. 457-459.
Walker, G. et al., "Increased remineralization of tooth enamel by milk containing added casein phosphopeptide-amorphous calcium phosphate", Journal of Dairy Research, vol. No. 73, 2006, pp. 74-78.
Walker, G.D. et al., "Consumption of milk with added casein phosphopeptide-amorphous calcium phosphate remineralizes enamel subsurface lesions in situ", Australian Dental Journal, vol. No. 54, Issue No. 3, Sep. 2009, pp. 245-249.
Walsh, L., "Tooth Mousse Information", GC Tooth Mousse Portfolio, 2nd Edition, Mar. 2005, 17 pages.
Walsh, L., "Topical CPP-ACP cremes beyond caries prevention", International Dentistry South Africa, vol. No. 4, Issue No. 5, 2014, pp. 26-32.
Walsh, L.J. et al., "Effect of CPP-ACP versus Potassium Nitrate on Cervical Dentinal Hypersensitivity", Abstract 0947, 84th General Session of the IADR, Jun. 28-Jul. 1, 2006, Brisbane, Australia, 1 page.
Walsh, L.J., "Application of the System for Total Environmental Management (STEM) to dysmineralization, dental erosion and tooth wear", Australasian Dental Practice, Jan./Feb. 2008, pp. 52-58.
Walsh, L.J., "The effects of GC Tooth Mousse on cervical dentinal sensitivity: a controlled clinical trial", International Dentistry SA—Australasian Edition, vol. No. 5, Issue No. 1, 2010, 7 pages.
Weiss, V., "Kariesprophylaxe in der kinderzahnärztlichen Praxis", ZWP, Oct. 2005, pp. 76-79 (English Abstract).
Westerman, G. et al., "Argon Laser and Remineralizing Paste Effect on Root Surface Caries", Abstract 0018, IADR, Mar. 2007, New Orleans, USA, 2 pages.
Westerman, G. et al., "Argon Laser and Remineralizing Paste with Fluoride Effects on Enamel Caries," AAPD, Washington, 2008, 1 page.

(56) References Cited

OTHER PUBLICATIONS

White DJ. "A 'return' to stannous fluoride dentifrices," J Clin Dent. 1995; 6 Spec No. 29-36.
White, D.J., "Use of Synthetic Polymer Gels for Artificial Carious Lesion Preparation", Caries Research, vol. No. 21, Issue No. 3, 1987, pp. 228-242.
Wikiel, K. et al, "Hydroxyapatite Mineralization and Demineralization in the Presence of Synthetic Phosphorylated Pentapeptides", Archives of Oral Biology, vol. No. 39, Issue No. 8, 1994, pp. 715-721.
Willershausen, B. et al., "In-Vitro-Studie Zur Überprufung einer möglichen Remineralisation durch caesinphosphopetidhaltige, amorphe Calciumphosphat-komplexe (CPP ACP)", Deutsche Zahnarztliche Zeitschrift, vol. No. 63, Issue No. 2, 2008, pp. 134-139 (Eng Abstract).
William, V. et al., "Molar Incisor Hypomineralization: Review and Recommendations for Clinical Management", Pediatric Dentistry, vol. No. 28, Issue No. 3, 2006, pp. 224-232.
Wong, L. et al., "Plaque microcosm biofilm mineralisation by CPP-ACP and calcium-phosphate-monofluorophosphate-urea mineralising solution", Abstract 1269, 84th General Session of the IADR, Jun. 28-Jul. 1, 2006, Brisbane, Australia, 1 page.
Wong, R. et al., "Incorporation of Casein Phosphopeptide-Amorphous Calcium Phosphate into a Temporary Cement", Abstract 0653, 84th General Session of the IADR, Jun. 28-Jul. 1, 2006, Brisbane, Australia, 1 page.
Wright, S. et al., "Artificial Caries Inhibited with MI Paste and Two Restorative Materials", Abstract 2777, IADR, 2007, New Orleans, USA, 2 pages.
Xie, Q. et al., "Remineralization Effects of CPP-ACP and Proanthocyanidin on Artificial Root Caries", Abstract 0512, IADR, 2007, New Orleans, USA, 2 pages.
Yamaguchi, K. et al., "Effect of CPP-ACP paste on mechanical properties of bovine enamel as determined by an ultrasonic device", Journal of Dentistry, vol. No. 34, 2006, pp. 230-236.
Yamaguchi, K. et al., "Ultrasonic Determination of the Effect of Casein Phosphopeptide-Amorphous Calcium Phosphate Paste on the Demineralization of Bovine Dentin", Caries Res, vol. No. 41, 2007, pp. 204-207.
Zanatta, F. et al., "Supragingival Plaque Removal with and without Dentifrice: A Randomized Controlled Clinical Trial", Braz Dent J, vol. No. 23, Issue No. 3, 2012, pp. 235-240.
Zero, D.T., "Dentifrices, mouthwashes, and remineralization/caries arrestment strategies", BMC Oral Health, vol. No. 6, Suppl. I:S9, Jul. 2006, 13 pages.
Zero, D.T., "In situ Caries Models", Adv Dent Res, vol. No. 9, Issue No. 3, Nov. 1995, pp. 214-230.
Zhang et al., "Antioxidant Properties of Casein Phosphopeptides (CPP) and Maillard-Type Conjugated Products," Antioxidants: 9 (8): 648 (Jul. 22, 2020) (14 pgs).
Zhang, L. et al., "Experimental Study of Phosphopeptide in Promoting Tooth Remineralization", Chin J Dent Res., vol. No. 3, Issue No. 1, May 2000, pp. 27-30.
Zhao, Q. et al., "The remineralization for enamel lesions by casein phosphopeptide-amorphous calcium fluoride phospate in vitro", Zhonghua Kou Qiang Yi Xue Za Zhi, vol. No. 36, Issue No. 6, 2001, 8 pages.

* cited by examiner

SEQUENCE LISTING

```
Sequence total quantity: 4
SEQ ID NO: 1            moltype = AA  length = 21
FEATURE                 Location/Qualifiers
VARIANT                 6
                        note = any naturally occurring amino acid
VARIANT                 8..10
                        note = any naturally occurring amino acid
VARIANT                 17
                        note = any naturally occurring amino acid
source                  1..21
                        mol_type = protein
                        organism = Bos sp.
SEQUENCE: 1
QMEAEXIXXX EEIVPNXVEQ K                                              21

SEQ ID NO: 2            moltype = AA  length = 25
FEATURE                 Location/Qualifiers
VARIANT                 15
                        note = any naturally occurring amino acid
VARIANT                 17..19
                        note = any naturally occurring amino acid
source                  1..25
                        mol_type = protein
                        organism = Bos sp.
SEQUENCE: 2
RELEELNVPG EIVEXLXXXE ESITR                                          25

SEQ ID NO: 3            moltype = AA  length = 25
FEATURE                 Location/Qualifiers
VARIANT                 11..13
                        note = any naturally occurring amino acid
VARIANT                 16
                        note = any naturally occurring amino acid
source                  1..25
                        mol_type = protein
                        organism = Bos sp.
SEQUENCE: 3
NANEEEYSIG XXXEEXAEVA TEEVK                                          25
```

-continued

```
SEQ ID NO: 4            moltype = AA  length = 21
FEATURE                 Location/Qualifiers
VARIANT                 8..10
                        note = any naturally occurring amino acid
VARIANT                 16
                        note = any naturally occurring amino acid
source                  1..21
                        mol_type = protein
                        organism = Bos sp.
SEQUENCE: 4
KNTMEHVXXX EESIIXQETY K                             21
```

FLUORIDE COMPOSITION AND METHODS FOR DENTAL MINERALIZATION

CROSS-REFERENCE TO RELATED APPLICATIONS

This application is a continuation of U.S. patent application Ser. No. 15/609,564, filed May 31, 2017, now U.S. Pat. No. 11,504,305, which is a continuation of U.S. patent application Ser. No. 12/162,683, filed Jul. 30, 2008, now U.S. Pat. No. 9,668,945, which is the National Stage of International Patent Application No. PCT/AU2007/000141, filed Feb. 9, 2007, which claims priority from Australian Patent Application Nos. 2006900634, filed Feb. 9, 2006, and 2006903531, filed Jun. 30, 2006.

SEQUENCE LISTING

The instant application contains a Sequence Listing which is being filed electronically in XML format and is hereby incorporated by reference in its entirety. Said XML copy, created on Sep. 20, 2023, is named Revised_SL_53232349.XML and is 8,055 bytes in size.

The present invention relates to a composition for mineralizing a dental surface, in particular tooth enamel. Methods of mineralizing hypomineralized lesions (including subsurface lesions) in the tooth enamel caused by dental caries, dental corrosion, erosion and fluorosis are also provided.

BACKGROUND

Dental caries is initiated by the demineralization of hard tissue of the teeth usually by organic acids produced from fermentation of dietary sugar by dental plaque odontopathogenic bacteria. Dental caries is still a major public health problem. Further, restored tooth surfaces can be susceptible to further dental caries around the margins of the restoration. Even though the prevalence of dental caries has decreased through the use of fluoride in most developed countries, the disease remains a major public health problem. Dental erosion or corrosion is the loss of tooth mineral by dietary or regurgitated acids. Dental hypersensitivity is due to exposed dentinal tubules through loss of the protective mineralized layer, cementum. Dental calculus is the unwanted accretion of calcium phosphate minerals on the tooth surface. All these conditions, dental caries, dental corrosion, dental hypersensitivity and dental calculus are therefore imbalances in the level of calcium phosphates.

Fluoride-containing dentifrices and mouthrinses have been demonstrated to significantly reduce caries experience in randomized, controlled clinical trials (Biesbrock et al., 1998; Biesbrock et al., 2001; Curnow et al., 2002; Davies et al., 2002; Biesbrock et al., 2003). The efficacy of these oral care products in reducing caries activity has been attributed to their ability to incorporate fluoride ions into plaque as several investigators have suggested an inverse relationship between plaque fluoride levels and caries incidence (Duckworth et al., 1992, Duckworth and Stewart, 1994, Hartshorne et al., 1994; Skold-Larsson et al., 2000; Lynch et al., 2004).

Fluoride ions in plaque immediately promote the formation of fluorhydroxyapatite in the presence of calcium and phosphate ions produced during demineralization of tooth enamel by plaque bacterial organic acids (ten Cate, 1999). This is now believed to be the major mechanism of fluoride ion's action in preventing enamel demineralization (ten Cate, 1999; Lynch et al., 2004). However, fluoride ions can also promote the remineralization of previously demineralized enamel if enough salivary or plaque calcium and phosphate ions are available when the fluoride is applied. For every two fluoride ions, ten calcium ions and six phosphate ions are required to form one unit cell of fluorapatite. Hence on topical application of fluoride ions, the availability of calcium and phosphate ions can be rate limiting for net enamel remineralization to occur. This is highly exacerbated under xerostomic (dry mouth) conditions. Furthermore, as fluoride treatments can lead to fluorosis, particularly in children, it would be advantageous to produce dental treatment compositions having the highest efficacy for the amount of fluoride present, to reduce the overall quantity of fluoride necessary to achieve the mineralization effect.

WO 98/40406 in the name of The University of Melbourne (the contents of which are herein incorporated fully by reference) describes casein phosphopeptide-amorphous calcium phosphate complexes (CPP-ACP) and CPP-stabilised amorphous calcium fluoride phosphate complexes (CPP-ACFP) which have been produced at alkaline pH. CPP-ACP (available commercially as Recaldent™) has been shown to remineralize enamel subsurface lesions in vitro and in situ (Reynolds, 1998; Shen et al., 2001; Reynolds et al., 2003).

The CPP which are active in forming the complexes do so whether or not they are part of a full-length casein protein. Examples of active (CPP) that can be isolated after tryptic digestion of full length casein have been specified in U.S. Pat. No. 5,015,628 and include peptides Bos $\alpha_{s1}$-casein X-5P (f59-79) [1], Bos β-casein X-4P (f1-25) [2], Bos $\alpha_{s2}$-casein X-4P (f46-70) [3] and Bos $\alpha_{s2}$-casein X-4P (f1-21) [4] as follows:

(SEQ ID NO: 1)
[1] Gln$^{59}$-Met-Glu-Ala-Glu-Ser(P)-Ile-Ser(P)-Ser(P)-Ser(P)-Glu-Glu-Ile-Val-Pro-Asn-Ser(P)-Val-Glu-Gln-Lys$^{79}$ $\alpha_{s1}$(59-79)

(SEQ ID NO: 2)
[2] Arg$^{1}$-Glu-Leu-Glu-Glu-Leu-Asn-Val-Pro-Gly-Glu-Ile-Val-Glu-Ser(P)-Leu-Ser(P)-Ser(P)-Ser(P)-Glu-Glu-Ser-Ile-Thr-Arg$^{25}$ β(1-25)

(SEQ ID NO: 3)
[3] Asn$^{46}$-Ala-Asn-Glu-Glu-Glu-Tyr-Ser-Ile-Gly-Ser(P)-Ser(P)-Ser(P)-Glu-Glu-Ser(P)-Ala-Glu-Val-Ala-Thr-Glu-Glu-Val-Lys$^{70}$ $\alpha_{s2}$(46-70)

(SEQ ID NO: 4)
[4] Lys$^{1}$-Asn-Thr-Met-Glu-His-Val-Ser(P)-Ser(P)-Ser(P)-Glu-Glu-Ser-Ile-Ile-Ser(P)-Gln-Glu-Thr-Tyr-Lys$^{21}$ $\alpha_{s2}$(1-21)

International patent application numbers WO 03/059303 and WO 03/059304 in the name of the Procter & Gamble Company identify difficulties in maintaining measurable fluoride ions levels in oral compositions containing CPP-ACP complexes and fluoride and propose including additional components to maintain measurable fluoride levels.

It would be useful augment the remineralization activity of CPP-ACP complexes or fluoride compositions to better treat conditions such as dental caries.

It is accordingly an object of the present invention to overcome, or at least alleviate, one or more of the difficulties and/or deficiencies related to the prior art.

SUMMARY OF THE INVENTION

In one aspect, the present invention provides a composition for dental mineralization including stabilized amorphous calcium phosphate (ACP) and a source of fluoride ions. The ACP may also contain some fluoride ions, and these fluoride ions may be part of a stabilised amorphous calcium fluoride phosphate (ACFP) complex.

The composition may include any suitable oral composition, such as a composition for maintaining oral/dental heath used by the patient and/or a treatment composition for use by the dental practitioner. Such compositions may include toothpastes, tooth gels, tooth powders, dental crèmes, liquid dentifrices, mouthwashes, troches, chewing gums, gingival massage crèmes, gargle tablets and dental restoratives.

In a further aspect of the present invention there is provided a method of mineralizing a dental surface or subsurface including providing a composition including stabilized ACP and a source of fluoride ions. In a preferred embodiment the dental surface is enamel.

In a further aspect of the present invention there is provided a method for treating and/or preventing dental caries including contacting a caries lesion in tooth enamel with a composition including stabilized ACP and a source of fluoride ions.

It has now been found that the dental remineralization efficacy of an oral composition including a source of fluoride ions can be substantially enhanced by the addition of stabilized ACP to the composition. Furthermore, the uptake of fluoride ions into dental enamel from an oral composition containing a source of fluoride ions can be enhanced by the inclusion of stabilized ACP into the composition.

Accordingly, in a further aspect of the present invention there is provided a method of increasing the remineralisation efficacy of an oral composition having a source of fluoride ions, including the incorporation of stabilized ACP into the oral composition.

In a further aspect of the present invention there is provided a method of increasing the uptake of fluoride ions into a dental surface or subsurface after treatment with an oral composition having a source of fluoride ions, including the incorporation of stabilized ACP into the oral composition.

Preferably, the dental surface or subsurface is tooth enamel.

In a further aspect, the present invention provides a method for increasing the uptake of fluoride ions into dental plaque after treatment with an oral composition having a source of fluoride ions, including the incorporation of stabilized ACP into the oral composition.

Typically in these methods of the invention, the fluoride ions are supplied separately but substantially simultaneously with the ACP.

The ACP is preferably a basic, soluble form of ACP.

The fluoride ions are preferably present in the composition in an amount greater than 1 ppm. More preferably, the amount is more than 3 ppm. In another embodiment, it is preferably more than 10 ppm. In typical embodiments described below, the amount may be several hundred or thousand ppm. The fluoride content is typically measured as a ppm in oral compositions in the manner commonly used in the art. Where the fluoride is provided from a source with the stabilized ACP, the ppm refers to the concentration of the fluoride in that source, typically a solution or suspension of bioavailable fluoride.

The fluoride ions may be from any suitable source. A source of fluoride ions may include free fluoride ions or fluoride salts. Examples of sources of fluoride ions include, but are not limited to the following: sodium fluoride, sodium monofluorophosphate, stannous fluoride, sodium silicofluoride and amine fluoride. These may be provided in solution (typically an aqueous solution), or a suspension.

Preferably the ACP is phosphopeptide (PP)-stabilized. Preferably, the phosphopeptide (as defined below) is a casein phosphopeptide. In a preferred embodiment the ACP is in the form of a casein phosphopeptide stabilized ACP complex.

In a further aspect of the present invention there is provided a method for mineralizing a tooth surface or subsurface comprising applying an ACP complex and a source of fluoride ions to a tooth surface or subsurface. Preferably the tooth surface or subsurface is tooth enamel. In a preferred embodiment, the tooth surface is tooth enamel containing a lesion selected from the group consisting of one or more of a caries lesion; a lesion caused by tooth erosion, a white spot lesion, or a fluorotic lesion.

In one embodiment, the dental surface is in need of such treatment. The invention also includes a method of treating a subject suffering dental caries, dentinal hypersensitivity, fluorosis or dental calculus.

It has been surprisingly found that the inclusion of stabilized ACP into an oral composition including a source of fluoride ions, increases extent to which remineralization occurs throughout the body of the enamel lesion, covering the surface and subsurface of the lesion, when compared with the oral composition without the stabilized ACP.

Accordingly, in a further aspect of the present invention there is provided a method for remineralizing a subsurface enamel lesion including contacting a subsurface enamel lesion with a composition including stabilized ACP and a source of fluoride ions.

In a further aspect there is provided the use of stabilized ACP and a source of fluoride ions in the manufacture of a medicament for the mineralization of a tooth surface or subsurface.

In a further aspect of the present invention there is provided the use of stabilized ACP and a source of fluoride ions in the manufacture of a composition for increasing the remineralization efficacy of an oral composition having a source of fluoride ions.

In a further aspect of the present invention there is provided the use of stabilized ACP and a source of fluoride ions in the manufacture of an oral composition for increasing the uptake of fluoride ions into a dental surface or subsurface after treatment with an oral composition having a source of fluoride ions.

In a further aspect of the present invention there is provided the use of stabilized ACP and a source of fluoride ions in the manufacture of an oral composition for increasing the uptake of fluoride ions into a dental plaque after treatment with an oral composition having a source of fluoride ions.

In a further aspect of the present invention there is provided the use of stabilized ACP and a source of fluoride ions in the manufacture of a composition for remineralizing a subsurface enamel lesion.

Without being bound by any theory or mode of action it is believed that the fluoride ions interact with the ACP to form fluorapatite on contact with the tooth surface, which is more resistant to acid challenge than normal tooth enamel. This may result in tooth enamel with superior caries resistant properties. Another part of the mechanism may involve the fluoride ions forming a PP stabilized amorphous calcium fluoride phosphate complex (which may include a mixture of basic amorphous calcium phosphate and fluoride ions, in situ during use). The use of amorphous calcium fluoride phosphate includes the use of a mixture of ACP with amorphous calcium fluoride phosphate.

"Phosphopeptide" or "PP" in the context of the description of this invention means an amino acid sequence in which at least one amino acid is phosphorylated. Preferably, the phosphopeptide includes one or more of the amino acid sequence -A-B-C-, where A is a phosphoamino residue, B is any amino acyl residue including a phosphoamino residue and C is selected from a glutamyl, aspartyl or phosphoamino residue. Any of the phosphoamino residues may independently be a phosphoseryl residue. B is desirably a residue the side-chain of which is neither relatively large nor hydrophobic. It may be Gly, Ala, Val, Met, Leu, Ile, Ser, Thr, Cys, Asp, Glu, Asn, Gln or Lys.

In another embodiment, at least two of the phosphoamino acids in the sequence are preferably contiguous. Preferably the phosphopeptide includes the sequence A-B-C-D-E, where A, B, C, D and E are independently phosphoserine, phosphothreonine, phosphotyrosine, phosphohistidine, glutamic acid or aspartic acid, and at least two, preferably three, of the A, B, C, D and E are a phosphoamino acid. In a preferred embodiment, the phosphoamino acid residues are phosphoserine, most preferably three contiguous phosphoserine residues. It is also preferred that D and E are independently glutamic or aspartic acid.

It will also be understood that the term "comprises" (or its grammatical variants) as used in this specification is equivalent to the term "includes" and may be used interchangeably and should not be taken as excluding the presence of other elements or features.

The ACP may also include ACFP, or ACFP may be included in the compositions and methods of the present invention in the place of ACP.

In one embodiment, the ACP or ACFP is stabilized by a casein phosphopeptide (CPP), which is in the form of intact casein or fragment of the casein, and the complex formed preferably has the formula $[CPP(ACP)_8]_n$ or $[(CPP)(ACFP)_8]_n$ where n is equal to or greater than 1, for example 6. The complex formed may be a colloidal complex, where the core particles aggregate to form large (eg 100 nm) colloidal particles suspended in water. Thus, the PP can be a casein protein or a polyphosphopeptide.

The PP may be from any source; it may be present in the context of a larger polypeptide, including a full length casein polypeptide, or it may be isolated by tryptic or other enzymatic or chemical digestion of casein, or other phosphoamino acid rich proteins such as phosphitin, or by chemical or recombinant synthesis, provided that it comprises the sequence -A-B-C- or A-B-C-D-E as described above. The sequence flanking this core sequence may be any sequence. However, those flanking sequences in $\alpha_{s1}$(59-79) [1], β(1-25) [2], $\alpha_{s2}$(46-70) [3] and $\alpha_{s2}$(1-21) [4] are preferred. The flanking sequences may optionally be modified by deletion, addition or conservative substitution of one or more residues. The amino acid composition and sequence of the flanking region are not critical. Examples of conservative substitutions are shown in Table 1 below.

TABLE 1

| Original Residue | Exemplary Conservative Substitution | Preferred Conservative Substitution |
|---|---|---|
| Ala | Val, Leu, Ile | Val |
| Asn | Gln Lys His Phe | Gln |
| Gln | Asn | Asn |
| Gly | Pro | Pro |
| Ile | Leu, Val, Met, Ala, Phe | Leu |
| Leu | Ile, Val, Met, Ala, Phe | Ile |
| Lys | Arg, Gln, Asn | Arg |
| Phe | Leu, Val, Ile, Ala | Leu |
| Pro | Gly | Gly |
| Ser | Thr | Thr |
| Val | Ile, Leu, Met, Phe, Ala | Leu |
| Asp | Glu | Glu |
| Thr | Ser | Ser |
| Trp | Tyr | Tyr |
| Tyr | Trp Phe Thr Ser | Phe |

The flanking sequences may also include non-naturally occurring amino acid residues. Commonly encountered amino acids which are not encoded by the genetic code, include:

2-amino adipic acid (Aad) for Glu and Asp;
2-aminopimelic acid (Apm) for Glu and Asp;
2-aminobutyric (Abu) acid for Met, Leu, and other aliphatic amino acids;
2-aminoheptanoic acid (Ahe) for Met, Leu and other aliphatic amino acids;
2-aminoisobutyric acid (Aib) for Gly;
cyclohexylalanine (Cha) for Val, and Leu and Ile;
homoarginine (Har) for Arg and Lys;
2, 3-diaminopropionic acid (Dpr) for Lys, Arg and His;
N-ethylglycine (EtGly) for Gly, Pro, and Ala;
N-ethylasparigine (EtAsn) for Asn, and Gln;
Hydroxyllysine (Hyl) for Lys;
allohydroxyllysine (AHyl) for Lys;
3-(and 4) hydroxyproline (3Hyp, 4Hyp) for Pro, Ser, and Thr;
alloisoleucine (Alle) for Ile, Leu, and Val;
ρ-amidinophenylalanine for Ala;
N-methylglycine (MeGly, sarcosine) for Gly, Pro, Ala.
N-methylisoleucine (Melle) for Ile;
Norvaline (Nva) for Met and other aliphatic amino acids;
Norleucine (Nle) for Met and other aliphatic amino acids;
Omithine (Om) for Lys, Arg and His;
Citrulline (Cit) and methionine sulfoxide (MSO) for Thr, Asn and Gln;
N-methylphenylalanine (MePhe), trimethylphenylalanine, halo (F, Cl, Br and I) phenylalanine, trifluorylphenylalanine, for Phe.

In one embodiment, the PP is one or more phosphopeptides selected from the group consisting of $\alpha_{s1}$(59-79) [1], β(1-25) [2], $\alpha_{s2}$(46-70) [3] and $\alpha_{s2}$(1-21) [4].

In preferred embodiments, the compositions of the present invention do not include a phosphate buffer and/or a calcium chelator.

In an embodiment of the present invention there is provided a composition for dental mineralization including stabilized amorphous calcium phosphate (ACP) and a source of fluoride ions, wherein the composition does not include a phosphate buffer and/or calcium chelator.

In another embodiment of the invention, the stabilised ACP complex is incorporated into an oral composition containing a source of fluoride ions such as toothpaste, mouth washes or formulations for the mouth to aid in the prevention and/or treatment of dental caries, tooth decay, dental erosion and/or fluorosis. The ACP complex may comprise 0.01-50% by weight of the composition, preferably 1.0-50%. For oral compositions, it is preferred that the amount of the ACP complex administered is 0.01-50% by weight, preferably 1.0%-50% by weight of the composition. In a particularly preferred embodiment, the oral composition of the present invention contains about 2% CPP-ACP. The fluoride ions may be present in the oral composition at a concentration in the range of about 200 ppm to 3000 ppm. In a preferred embodiment, the fluoride ions are at a concentration in the range of about 400 ppm to about 1500 ppm. In a further preferred embodiment, the fluoride ions in the oral composition are at a concentration of about 900 ppm.

An oral composition of this invention which contains the above-mentioned agents may be prepared and used in various forms applicable to the mouth such as dentifrice including toothpastes, toothpowders and liquid dentifrices, mouthwashes, troches, chewing gums, dental pastes, gingival massage creams, gargle tablets, dairy products and other foodstuffs. An oral composition according to this invention may further include additional well known ingredients depending on the type and form of a particular oral composition.

In certain preferred forms of the invention the oral composition may be substantially liquid in character, such as a mouthwash or rinse. In such a preparation the vehicle is typically a water-alcohol mixture desirably including a humectant as described below. Generally, the weight ratio of water to alcohol is in the range of from about 1:1 to about 20:1. The total amount of water-alcohol mixture in this type of preparation is typically in the range of from about 70 to about 99.9% by weight of the preparation. The alcohol is typically ethanol or isopropanol. Ethanol is preferred.

The pH of such liquid and other preparations of the invention is generally in the range of from about 5 to about 9 and typically from about 5.0 to 7.0. The pH can be controlled with acid (e.g. citric acid or benzoic acid) or base (e.g. sodium hydroxide) or buffered (as with sodium citrate, benzoate, carbonate, or bicarbonate, disodium hydrogen phosphate, sodium dihydrogen phosphate, etc).

In other desirable forms of this invention, the stabilised ACP composition may be substantially solid or pasty in character, such as toothpowder, a dental tablet or a toothpaste (dental cream) or gel dentifrice. The vehicle of such solid or pasty oral preparations generally contains dentally acceptable polishing material. Examples of polishing materials are water-insoluble sodium metaphosphate, potassium metaphosphate, tricalcium phosphate, dihydrated calcium phosphate, anhydrous dicalcium phosphate, calcium pyrophosphate, magnesium orthophosphate, trimagnesium phosphate, calcium carbonate, hydrated alumina, calcined alumina, aluminium silicate, zirconium silicate, silica, bentonite, and mixtures thereof. Other suitable polishing material include the particulate thermosetting resins such as melamine-, phenolic, and urea-formaldehydes, and cross-linked polyepoxides and polyesters. Preferred polishing materials include crystalline silica having particle sizes of up to about 5 microns, a mean particle size of up to about 1.1 microns, and a surface area of up to about 50,000 $cm^2/g$, silica gel or colloidal silica, and complex amorphous alkali metal aluminosilicate.

When visually clear gels are employed, a polishing agent of colloidal silica, such as those sold under the trademark SYLOID as Syloid 72 and Syloid 74 or under the trademark SANTOCEL as Santocel 100, alkali metal aluminosilicate complexes are particularly useful since they have refractive indices close to the refractive indices of gelling agent-liquid (including water and/or humectant) systems commonly used in dentifrices.

Many of the so-called "water insoluble" polishing materials are anionic in character and also include small amounts of soluble material. Thus, insoluble sodium metaphosphate may be formed in any suitable manner, for example as illustrated by Thorpe's Dictionary of Applied Chemistry, Volume 9, 4th Edition, pp. 510-511. The forms of insoluble sodium metaphosphate known as Madrell's salt and Kurrol's salt are further examples of suitable materials. These metaphosphate salts exhibit only a minute solubility in water, and therefore are commonly referred to as insoluble metaphosphates (IMP). There is present therein a minor amount of soluble phosphate material as impurities, usually a few percent such as up to 4% by weight. The amount of soluble phosphate material, which is believed to include a soluble sodium trimetaphosphate in the case of insoluble metaphosphate, may be reduced or eliminated by washing with water if desired. The insoluble alkali metal metaphosphate is typically employed in powder form of a particle size such that no more than 1% of the material is larger than 37 microns.

The polishing material is generally present in the solid or pasty compositions in weight concentrations of about 10% to about 99%. Preferably, it is present in amounts from about 10% to about 75% in toothpaste, and from about 70% to about 99% in toothpowder. In toothpastes, when the polishing material is silicious in nature, it is generally present in an amount of about 10-30% by weight. Other polishing materials are typically present in amount of about 30-75% by weight.

In a toothpaste, the liquid vehicle may comprise water and humectant typically in an amount ranging from about 10% to about 80% by weight of the preparation. Glycerine, propylene glycol, sorbitol and polypropylene glycol exemplify suitable humectants/carriers. Also advantageous are liquid mixtures of water, glycerine and sorbitol. In clear gels where the refractive index is an important consideration, about 2.5-30% w/w of water, 0 to about 70% w/w of glycerine and about 20-80% w/w of sorbitol are preferably employed.

Toothpaste, creams and gels typically contain a natural or synthetic thickener or gelling agent in proportions of about 0.1 to about 10, preferably about 0.5 to about 5% w/w. A suitable thickener is synthetic hectorite, a synthetic colloidal magnesium alkali metal silicate complex clay available for example as Laponite (e.g. CP, SP 2002, D) marketed by Laporte Industries Limited. Laponite D is, approximately by weight 58.00% $SiO_2$, 25.40% MgO, 3.05% $Na_2O$, 0.98% $Li_2O$, and some water and trace metals. Its true specific gravity is 2.53 and it has an apparent bulk density of 1.0 g/ml at 8% moisture.

Other suitable thickeners include Irish moss, iota carrageenan, gum tragacanth, starch, polyvinylpyrrolidone, hydroxyethylpropylcellulose, hydroxybutyl methyl cellulose, hydroxypropyl methyl cellulose, hydroxyethyl cellulose (e.g. available as Natrosol), sodium carboxymethyl cellulose, and colloidal silica such as finely ground Syloid (e.g. 244). Solubilizing agents may also be included such as humectant polyols such propylene glycol, dipropylene glycol and hexylene glycol, cellosolves such as methyl cellosolve and ethyl cellosolve, vegetable oils and waxes containing at least about 12 carbons in a straight chain such as olive oil, castor oil and petrolatum and esters such as amyl acetate, ethyl acetate and benzyl benzoate.

It will be understood that, as is conventional, the oral preparations will usually be sold or otherwise distributed in suitable labelled packages. Thus, a bottle of mouth rinse will have a label describing it, in substance, as a mouth rinse or mouthwash and having directions for its use; and a toothpaste, cream or gel will usually be in a collapsible tube, typically aluminium, lined lead or plastic, or other squeeze, pump or pressurized dispenser for metering out the contents, having a label describing it, in substance, as a toothpaste, gel or dental cream.

Organic surface-active agents may be used in the compositions of the present invention to achieve increased prophylactic action, assist in achieving thorough and complete dispersion of the active agent throughout the oral cavity, and render the instant compositions more cosmetically acceptable. The organic surface-active material is preferably anionic, non-ionic or ampholytic in nature and preferably does not interact with the active agent. It is preferred to employ as the surface-active agent a detersive material which imparts to the composition detersive and foaming properties. Suitable examples of anionic surfactants are water-soluble salts of higher fatty acid monoglyceride monosulfates, such as the sodium salt of the monosulfated monoglyceride of hydrogenated coconut oil fatty acids, higher alkyl sulfates such as sodium lauryl sulfate, alkyl aryl sulfonates such as sodium dodecyl benzene sulfonate, higher alkylsulfo-acetates, higher fatty acid esters of 1,2-dihydroxy propane sulfonate, and the substantially saturated higher aliphatic acyl amides of lower aliphatic amino carboxylic acid compounds, such as those having 12 to 16 carbons in the fatty acid, alkyl or acyl radicals, and the like. Examples of the last mentioned amides are N-lauroyl sarcosine, and the sodium, potassium, and ethanolamine salts of N-lauroyl, N-myristoyl, or N-palmitoyl sarcosine which should be substantially free from soap or similar higher fatty acid material. The use of these sarconite compounds in the oral compositions of the present invention is particularly advantageous since these materials exhibit a prolonged marked effect in the inhibition of acid formation in the oral cavity due to carbohydrates breakdown in addition to exerting some reduction in the solubility of tooth enamel in acid solutions. Examples of water-soluble non-ionic surfactants suitable for use are condensation products of ethylene oxide with various reactive hydrogen-containing compounds reactive therewith having long hydrophobic chains (e.g. aliphatic chains of about 12 to 20 carbon atoms), which condensation products ("ethoxamers") contain hydrophilic polyoxyethylene moieties, such as condensation products of poly (ethylene oxide) with fatty acids, fatty alcohols, fatty amides, polyhydric alcohols (e.g. sorbitan monostearate) and polypropyleneoxide (e.g. Pluronic materials).

The surface active agent is typically present in amount of about 0.1-5% by weight. It is noteworthy, that the surface active agent may assist in the dissolving of the active agent of the invention and thereby diminish the amount of solubilizing humectant needed.

Various other materials may be incorporated in the oral preparations of this invention such as whitening agents, preservatives, silicones, chlorophyll compounds and/or ammoniated material such as urea, diammonium phosphate, and mixtures thereof. These adjuvants, where present, are incorporated in the preparations in amounts which do not substantially adversely affect the properties and characteristics desired.

Any suitable flavouring or sweetening material may also be employed. Examples of suitable flavouring constituents are flavouring oils, e.g. oil of spearmint, peppermint, wintergreen, *sassafras*, clove, sage, *eucalyptus*, marjoram, cinnamon, lemon, and orange, and methyl salicylate. Suitable sweetening agents include sucrose, lactose, maltose, sorbitol, xylitol, sodium cyclamate, perillartine, AMP (aspartyl phenyl alanine, methyl ester), saccharine, and the like. Suitably, flavour and sweetening agents may each or together comprise from about 0.1% to 5% more of the preparation.

The compositions of this invention can also be incorporated in lozenges, or in chewing gum or other products, e.g. by stirring into a warm gum base or coating the outer surface of a gum base, illustrative of which are jelutong, rubber latex, vinylite resins, etc., desirably with conventional plasticizers or softeners, sugar or other sweeteners or such as glucose, sorbitol and the like.

In a further aspect, the invention provides compositions including pharmaceutical compositions comprising the ACP complex described above and a source of fluoride ions together with a pharmaceutically-acceptable carrier. Such compositions may be selected from the group consisting of dental, anticariogenic compositions and therapeutic compositions. Dental compositions or therapeutic compositions may be in the form of a gel, liquid, solid, powder, cream or lozenge. Therapeutic compositions may also be in the form of tablets or capsules. For example, a crème formulation may be employed containing: water; glycerol; CPP-ACP; sodium fluoride, D-sorbitol; silicon dioxide; sodium carboxymethylcellulose (CMC-Na); propylene glycol; titanium dioxide; xylitol; phosphoric acid; guar gum; zinc oxide; sodium saccharin; ethyl p-hydroxybenzoate; magnesium oxide; butyl p-hydroxybenzoate and propyl p-hydroxybenzoate.

The invention further includes a formulation described above provided together with instructions for its use to treat or prevent any one or more of dental caries or tooth decay, dental corrosion and fluorosis.

In a further aspect, the present invention provides a kit of parts including (a) a source of fluoride ions and (b) a CPP-ACP complex in a pharmaceutically acceptable carrier. Desirably, the kit further includes instructions for their use for the mineralization of a dental surface in a patent in need of such treatment. In one embodiment, the agent and the complex are present in suitable amounts for treatment of a patient. The invention also provides a system for improved remineralization including (a) a source of fluoride ions and (b) a CPP-ACP complex in a pharmaceutically acceptable carrier for combining with the source of fluoride before application to a dental surface.

In a further aspect, the present invention provides a method for enhancing the remineralization effect of fluoride ions in an oral care composition including addition of stabilised ACP to the oral care composition.

In a further aspect, the present invention provides a method of improving fluoride incorporation into an enamel lesion including contacting a lesion in tooth enamel with a composition including stabilized ACP and a source of fluoride ions.

In a further aspect of the present invention there is provided the use of stabilized ACP and a source of fluoride ions in the manufacture of a medicament for the mineralization of a dental surface or subsurface.

In a further aspect of the present invention there is provided the use of stabilized ACP and a source of fluoride ions in the manufacture of a medicament for the treatment and/or prevention of dental caries.

In a further aspect of the present invention there is provided a method for treating and/or preventing dental erosion comprising contacting a lesion in tooth enamel caused by erosion with a composition including stabilized ACP and a source of fluoride ions.

In a further aspect of the present invention there is provided the use of stabilized ACP and a source of fluoride ions in the manufacture of a medicament for the treatment and/or prevention of dental erosion.

It will be clearly understood that, although this specification refers specifically to applications in humans, the invention is also useful for veterinary purposes. Thus in all aspects the invention is useful for domestic animals such as cattle, sheep, horses and poultry; for companion animals such as cats and dogs; and for zoo animals.

The invention will now be further described with reference to the following non-limiting examples and FIGURES.

In the FIGURES, 1 shows representative microradiographs of enamel subsurface lesions after remineralization in situ and acid challenge (AC) in vitro.

EXAMPLE 1

A plaque fluoride study was conducted as a randomized, double-blind three-way cross-over design involving three coded mouthrinses. The three mouthrinses were (i) 2% w/v CPP-ACP (Recaldent™) as supplied by Recaldent Pty Ltd (Melbourne, Australia) and 450 ppm F as NaF in deionized water, (ii) 450 ppm F as NaF in deionized water, (iii) a placebo control rinse as deionized water. The CPP-ACP mouthrinse was adjusted to pH 7.0 with 1M HCl. Subjects were supplied with the coded rinses in opaque plastic tubes and used 15 ml of each rinse for 60 s three times a day, after breakfast, after lunch and at night before retiring, for four days and kept a diary of mouthrinse use. On the fifth day the rinse was used after breakfast and supragingival plaque was collected 2-3 hr later. Subjects refrained from all oral hygiene procedures while using the rinses. Each subject crossed over to use each mouthrinse with a four week washout period between treatments. Supragingival plaque was collected using a Gracey 7/8 curette from the buccal and lingual surfaces of all teeth. Plaque was collected into a preweighed microcentrifuge tube, re-weighed and then stored at −70° C. After thawing of the plaque samples they were centrifuged for 5 min at 20,000 g, dried in a Jouan RC10.10 rotary evaporator and then re-weighed to determine dry weights. The dry samples were then extracted with 200 μl of 1M HCl by mixing in a vortex mixer for 1 min and then treated in ice water in a Bransonic 12 ultrasonic bath (Consolidated Ultrasonic, Melbourne, Australia) for 8 h. After centrifugation (20,000 g, 5 min) fluoride ion concentrations in the supernatant were determined as described previously (Silva and Reynolds, 1996). The plaque fluoride levels were statistically analyzed using a non-parametric Friedmans test with Wilcoxon Signed-Ranks tests (Norusis, 1993).

Both fluoride rinses produced an increase in plaque fluoride levels with the 450 ppm fluoride rinse nearly doubling the fluoride level obtained with the placebo control rinse (Table 2). The addition of 2% CPP-ACP to the 450 ppm fluoride rinse significantly increased the incorporation of fluoride ions into plaque where the plaque fluoride level was over double that obtained with the fluoride rinse. No significant difference was observed in the dry weights of plaque for the three rinses, however the dry weight of the plaque obtained with the 2% CPP-ACP plus 450 ppm fluoride rinse exhibited a tendency to be greater than that obtained with the other two rinses.

TABLE 2

Fluoride levels in supragingival plaque after treatment with various mouthrinses

| Mouthrinse | Plaque Fluoride Level (nmol/mg dry wt) | Dry Weight of Plaque (mg) |
|---|---|---|
| Placebo Control | 7.4 ± 4.7[a,b] | 4.3 ± 2.5[a] |
| Fluoride (450 ppm) | 14.4 ± 6.7[a,b] | 3.9 ± 1.9[a] |
| 2% CPP-ACP plus 450ppm F | 33.0 ± 17.6[a,b] | 5.0 ± 2.1[a] |

[a]Mean ± SD (n = 14).
[b]Significantly different from all values in same column ($P < 0.001$).

EXAMPLE 2

A remineralization study was conducted as a randomized, double-blind, 5-way crossover remineralization study with five toothpaste slurries using an in situ model previously described (Shen et al., 2001; Reynolds et al., 2003). Palatal appliances containing six human enamel half-slabs with subsurface demineralized lesions were prepared as described by Shen et al. (2001). Toothpastes were prepared as coded products and the base of the product consisted of sorbitol, silica, sodium lauryl sulphate, flavour, sodium carboxymethyl cellulose, titanium dioxide, xanthan gum, sodium saccharin and water. The pH of the formulation was adjusted to 7.0 with phosphoric acid. Five toothpaste formulations were prepared: (i) placebo, (ii) 1100 ppm fluoride as sodium fluoride, (iii) 2800 ppm fluoride as sodium fluoride, (iv) 2% CPP-ACP and (v) 2% CPP-ACP plus 1100 ppm fluoride as sodium fluoride. Toothpaste slurries were prepared by adding 1 g of paste to 4 ml deionized water and vortex mixing for 60 s. Subjects rinsed with the slurries for 60 s four times per day for 14 days at the following times: 10.00 am, 11.30 am, 2.00 pm and 3.30 pm. Subjects kept diaries of toothpaste slurry use and were instructed not to eat, drink or perform oral hygiene procedures while wearing the appliances. When the appliances were not in the mouth they were stored in a sealed moist plastic bag at room temperature. Subjects were instructed to rinse their appliances using deionized water. After the completion of each treatment the enamel half-slabs were removed from the appliances and prepared for acid challenge.

For the acid challenge of the remineralized lesions, the test enamel blocks were covered with acid-resistant nail varnish to leave only half of each remineralized window ($1\times3$ $mm^2$) exposed. The slabs were mounted onto the end of 3-4 cm sticks of dental wax and immersed in 40 ml of unagitated lactic/Carbopol demineralization buffer (Reynolds, 1997) for 8 hours at 37° C. After completion of this acid challenge the enamel slabs were rinsed with deionized water and sectioned through the midline of both windows to produce two blocks. These two enamel blocks containing remineralized lesions and acid challenged remineralized lesions were paired with their control block containing the original demineralized lesions and embedded, sectioned and microradiographed as described previously (Shen et al., 2001). Images of the lesions and the neighbouring sound enamel were scanned and the percent mineral profile of each lesion determined as described by Iijima et al. (2004). The difference between the areas under the densitometric profile of the original demineralized lesion and sound enamel, calculated by trapezoidal integration, is represented by $\Delta Zd$. The difference between the areas under the densitometric profile of the remineralized lesion and sound enamel, calculated by trapezoidal integration, is represented by ΔZr. Percentage remineralization (% R) represents the percentage change in ΔZ values eg $$\% R - \frac{\Delta Zd - \Delta Xr}{\Delta Zd} \times 100$$

(Iljima et al., 2004). Data were statistically analyzed using a repeated measures ANOVA with post hoc Scheffe test (Norusis, 1993).

All toothpaste formulations replaced mineral in the enamel subsurface lesions in the in situ study (Table 3). Fluoride produced a dose-response remineralization with the 2800 ppm replacing significantly more mineral than the 1100 ppm formulation which replaced significantly more than the placebo control. The toothpaste with 2% CPP-ACP produced a level of remineralization similar to the 2800 ppm fluoride formulation and the paste with 2% CPP-ACP plus 1100 ppm fluoride was superior to all other formulations including the 2800 ppm fluoride paste. Microradiography of the lesions after remineralization revealed that fluoride ion alone tended to promote remineralization of the surface layer whereas CPP-ACP promoted remineralization, even in the presence of fluoride, throughout the body of the lesion (FIG. 1).

Acid challenge in vitro of the in situ remineralized enamel slabs resulted in substantial loss of mineral from the placebo-treated enamel slabs. A smaller amount of mineral was lost from the lesions remineralized with 2% CPP-ACP upon acid challenge. Although there was a tendency to lose a small amount of mineral from the enamel treated with the fluoride formulations the loss was not statistically significant. The residual remineralization after acid challenge was significantly greater for the paste containing 2% CPP-ACP plus 1100 ppm fluoride when compared with the residual remineralization obtained with all other pastes including the paste containing 2800 ppm fluoride. Microradiography of the remineralized lesions after acid challenge revealed that the acid removed mineral predominantly from underneath the remineralized zone.

This in situ study showed a clear dose response in enamel subsurface lesion remineralization by fluoride, with 8.2±0.2% remineralization by the toothpaste containing 1100 ppm F– and 15.5±2.4% by that containing 2800 ppm F–. It also revealed that the paste containing 2% CPP-ACP was superior in remineralizing enamel subsurface lesions when compared with the paste containing 1100 ppm F– and was not significantly different to the paste containing 2800 pm F. The paste containing 2% CPP-ACP plus 1100 ppm F– produced greater remineralization than the paste containing 2800 ppm F–. Addition of 2% CPP-ACP to 1100 ppm F– increased enamel subsurface remineralization by 156% relative to the 1100 ppm F– paste.

The casein phosphopeptides (CPP) have been shown to not only stabilize amorphous calcium phosphate (ACP), but also to deliver and localize ACP at the tooth surface (Reynolds, 1998; Reynolds et al., 1999; Reynolds et al., 2003). CPP-ACP in a mouthwash significantly increased the level of calcium and inorganic phosphate ions in supragingival plaque with the CPP bound to salivary pellicle and to the surface of bacteria in the supragingival plaque biofilm (Reynolds et al., 2003). This clinical trial demonstrated that CPP-ACP can also promote the uptake of fluoride ions into plaque. Therefore CPP-ACP should promote the uptake of calcium, phosphate and fluoride ions into supragingival plaque when added to a fluoride-containing toothpaste formulation. The present in situ study demonstrated that CPP-ACP delivered in a toothpaste formulation was very effective in enamel subsurface remineralization, and that the mineral formed was more resistant to acid than natural enamel apatite. Enamel remineralized by CPP-ACP in the presence of fluoride showed greater resistance to acid challenge relative to natural enamel or enamel remineralized by CPP-ACP. This suggests that CPP-ACP in the presence of F– ions promotes remineralization with acid-resistant fluorapatite. These results demonstrate that addition of CPP-ACP, to a toothpaste formulation significantly enhances the ability of fluoride to remineralize enamel subsurface lesions with acid resistant fluorapatite.

TABLE 3

Percentage remineralization of enamel subsurface lesions by various toothpaste formulations followed by acid challenge

| | Placebo control | 1100 ppm fluoride | 2800 ppm fluoride | 2% CPP-ACP | 2% CPP-ACP plus 1100 ppm fluoride |
|---|---|---|---|---|---|
| Initial lesion depth (μm) | 105 ± 7[a] | 106 ± 9 | 102 ± 7 | 107 ± 8 | 104 ± 8 |
| ΔZd (vol % min. μm) | 4,489 ± 2,465 | 3,544 ± 1,432 | 3,704 ± 1,278 | 4,287 ± 2,282 | 4,382 ± 1,714 |
| ΔZd − AZr | 138 ± 122[d] | 290 ± 136[d] | 576 ± 222 | 580 ± 311 | 919 ± 462[d] |
| % R[b] | 3.1 ± 1.6[e] | 8.2 ± 2.0[e] | 15.5 ± 2.4 | 13.5 ± 1.5 | 21.0 ± 5.9[e] |
| % $R_{AC}$[c] | −4.1 ± 1.6[f,g] | 7.1 ± 1.3[f] | 13.2 ± 1.1[f] | 8.7 ± 1.5[f,g] | 17.4 ± 1.2[f] |

[a]Mean + SD (n = 14).
[b]% R = ΔZd − ΔZr/ΔZd × 100 (Shen et al., 2001).
[c]$R_{AC}$ = % R after acid challenge.
[d]significantly different from all other values in row (P < 0.01).
[e]significantly different from all other values in row (P < 0.01).
[f]significantly different from all other values in row (P < 0.01).
[g]significantly different from % R value in same column (P < 0.01).

EXAMPLE 3

Electron microprobe wavelength dispersive spectrometry was used to measure fluoride levels in remineralized lesions as follows.

Enamel sections were embedded in epoxy resin on a one inch specimen holder. The resin was flat polished to expose the enamel sections using 2400 grit abrasive paper. To achieve optical smoothness 3 μm and 1 μm diamond polishing pastes were used on a cloth pad with final finishing accomplished with a 0.25 μm aluminium oxide paste. All samples and standards were coated with 20 nm of carbon using a Dynavac 300. The electron probe (8900R Super-Probe JEOL, Japan) was operated at a 15 kV accelerating voltage, 12 nA specimen current, 40° take-off angle. Dwell times of 10 seconds for the peak and 10 seconds for the background per point were used. The detection limit for F was 800 ppm. The beam diameter employed during collection of standards was a 10 μm spot whereas the diameter for analysis of lesions was 2 μm. Calcium, phosphorous, fluoride, and chloride X-ray intensities were measured simultaneously using four spectrometers with filter crystals of Pentaerythritol, Pentaerythritol, W/Si layered synthetic, Pentaerythritol, respectively. The standard was analysed using a 10 μm (defocused) and 2 μm (focused) diameter beam to calibrate the X ray count intensity. The standard was synthetic fluorapatite with a calcium to phosphorous ratio of 1.667 and a fluoride content of 3.70 wt %. Elemental maps and quantitative line scans for calcium, phosphorous, fluoride, oxygen and chlorine were collected across the lesions starting from the base of the lesion to the surface layer. Data was corrected using a Phi(RhoZ)-Parabolic method correction procedure implemented in STRATA (Thin Film Analysis Package).

Microradiography of the remineralized lesions after acid challenge revealed that the acid removed mineral predominantly from underneath the remineralized zone. The fluoride level of the remineralized lesions for the placebo, 1100 ppmF and 2% CPP-ACP plus 1100 ppmF pastes was determined using electron microprobe wavelength dispersive spectrometry (Table 4). The fluoride incorporated into the lesion was significantly higher for the 2% CPP-ACP plus 1100 ppmF paste when compared with the 1100 ppmF paste (Table 4). Further, the measured fluoride levels for the 2% CPP-ACP plus 1100 ppmF paste was close to that predicted assuming the remineralized mineral was fluorapatite (Table 4).

TABLE 4

Predicted and measured fluoride levels in the remineralized lesions

| Toothpaste | Remineralization level (vol % min) | Predicted[a] F (wt %) | Measured[b] F (wt %) |
|---|---|---|---|
| Placebo | 1.31 | 0.05 | 0.05 ± 0.05[c] |
| 1100 ppmF | 2.74 | 0.10 | 0.23 ± 0.09[c] |
| CPP-ACP 2% plus 1100 ppmF | 8.84 | 0.33 | 0.30 ± 0.13[c] |

[a]Predicted F level based on remineralized mineral being fluorapatite (3.768 wt % F)
[b]Measured using electron microprobe wavelength dispersive spectrometry with a JEOL 8900 SuperProbe microprobe. Mean level of fluoride measured by line scans from the base of the lesion to the surface layer.
[c]Significantly different from other values in same column ($p < 0.01$).

EXAMPLE 4

A topical crème may be produced in accordance with the present invention having the following ingredients:

Water
glycerol
CPP-ACP complexes
D-sorbitol
sodium carboxymethylcellulose (CMC-Na)
propylene glycol
silicon dioxide
titanium dioxide
xylitol
phosphoric acid
sodium fluoride
flavouring
sodium saccharin
ethyl p-hydroxybenzoate
propyl p-hydroxybezoate
butyl p-hydroxybenzoate

EXAMPLE 5

A mouthrinse formulation be produced in accordance with the present invention having the following composition:

Water
Alcohol
Poloxamer 407
Sodium Lauryl Sulphate
CPP-ACP complexes
Sodium Fluoride
Flavours
Sodium Saccharin
Ethyl p-hydroxybenzoate
Propyl p-hydroxybenzoate
Butyl p-hydroxybenzoate

EXAMPLE 6

A sugar-free chewing gum formulation be produced in accordance with the present invention having the following composition:

Crystalline sorbitol/mannitol/xylitol
Gum base
Calcium carbonate
Glycerine
CPP-ACP complexes
Sodium Fluoride
Flavour oil
Water It will be understood that the invention disclosed and defined in this specification extends to all alternative combinations of two or more of the individual features mentioned or evident from the text or drawings. All of these different combinations constitute various alternative aspects of the invention.

REFERENCES

Biesbrock A R, Faller R V, Bartizek R D, Court L K, McClanahan S F (1998). Reversal of incipient and radiographic caries through the use of sodium and stannous fluoride dentifrices in a clinical trial. J Clin Dent 9:5-10.

Biesbrock A R, Gerlach R W, Bollmer B W, Faller R V, Jacobs S A, Bartizek R D (2001). Relative anti-caries efficacy of 1100, 1700, 2200, and 2800 ppm fluoride ion in a sodium fluoride dentifrice over 1 year. Community Dent Oral Epidemiol 29:382-389.

Biesbrock A R, Bartizek R D, Gerlach R W, Jacobs S A, Archila L (2003). Dose response efficacy of sodium fluoride dentifrice at 9 and 21 months with supervised brushing. Am J Dent 16:305-312.

Cross K J, Huq N L, Palamara J E, Perich J W, Reynolds E C (2005). Physicochemical characterization of casein phosphopeptide-amorphous calcium phosphate nanocomplexes. J Biol Chem 280:15362-15369.

Curnow M M, Pine C M, Burnside G, Nicholson J A, Chesters R K, Huntington E (2002). A randomised controlled trial of the efficacy of supervised toothbrushing in high-caries-risk children. Caries Res 36:294-300.

Davies G M, Worthington H V, Ellwood R P, Bentley E M, Blinkhom A S, Taylor G O, et al. (2002). A randomised controlled trial of the effectiveness of providing free fluoride toothpaste from the age of 12 months on reducing caries in 5-6 year old children. Community Dent Health 19:131-136.

Duckworth R M, Morgan S N, Gilbert R J (1992). Oral fluoride measurements for estimation of the anti-caries efficacy of fluoride treatments. J Dent Res 71 Spec No: 836-840.

Duckworth R M, Stewart D (1994). Effect of mouthwashes of variable NaF concentration but constant NaF content on oral fluoride retention. Caries Res 28:43-47.

Hartshorne J E, Grobler S R, Louw A J, Carstens I L, Laubscher J A (1994). The relationship between plaque index scores, fluoride content of plaque, plaque pH, dental caries experience and fluoride concentration in drinking water in a group of primary school children. J Dent Assoc S Afr 49:5-10.

Iijima Y, Cai F, Shen P, Walker G, Reynolds C, Reynolds E C (2004). Acid resistance of enamel subsurface lesions remineralized by a sugar-free chewing gum containing casein phosphopeptide-amorphous calcium phosphate. Caries Res 38:551-6.

Lynch R J, Navada R, Walia R (2004). Low-levels of fluoride in plaque and saliva and their effects on the demineralisation and remineralisation of enamel; role of fluoride toothpastes. Int Dent J:304-309.

Norusis M (1993). SPSS for Windows: Base System User's Guide, Release 6.0 Illinois, USA: SPSS INC.

Reynolds E C, Cain C J, Webber F L, Black C L, Riley P F, Johnson I H, et al. (1995). Anticariogenicity of calcium phosphate complexes of tryptic casein phosphopeptides in the rat. J Dent Res 74:1272-1279.

Reynolds E C (1997). Remineralization of enamel subsurface lesions by casein phosphopeptide-stabilized calcium phosphate solutions. J Dent Res 76:1587-1595.

Reynolds E C (1998). Anticariogenic complexes of amorphous calcium phosphate stabilised by casein phosphopeptides. Invited review. Spec Care Dentist 18:8-16.

Reynolds E C, Black C L, Cai F, Cross K J, Eakins D, Huq N L, et al. (1999). Advances in enamel remineralization: casein phosphopeptide-amorphous calcium phosphate. J Clin Dent X:86-88.

Reynolds E C, Cai F, Shen P, Walker G D (2003). Retention in plaque and remineralization of enamel lesions by various forms of calcium in a mouthrinse or sugar-free chewing gum. J Dent Res 82:206-211.

Shen P, Cai F, Nowicki A, Vincent J, Reynolds E C (2001). Remineralization of enamel subsurface lesions by sugar-free chewing gum containing casein phosphopeptide-amorphous calcium phosphate. J Dent Res 80:2066-2070.

Silva M, Reynolds E C (1996). Fluoride content of infant formula in Australia. Aust Dent J 41:37-42.

Skold-Larsson K, Modeer T, Twetman S (2000). Fluoride concentration in plaque in adolescents after topical application of different fluoride varnishes. Clin Oral Investig 4:31-34.

ten Cate J M (1999). Current concepts on the theories of the mechanism of action of fluoride. Acta Odontol Scand 57:325-329.

The invention claimed is:

1. A composition comprising (i) about 0.01% to 50% by weight casein phosphopeptide-stabilized amorphous calcium phosphate or casein phosphopeptide-stabilized amorphous calcium fluoride phosphate, and, separately, (ii) free fluoride ions in an amount of from at least 400 ppm to about 3,000 ppm, and wherein the composition does not include a calcium chelator and does not include an additional phosphate buffer.

2. The composition according to claim 1, wherein the composition comprises sodium fluoride.

3. The composition according to claim 1, wherein the free fluoride ions are provided by sodium fluoride, stannous fluoride, amine fluoride and combinations thereof.

4. The composition according to claim 1, wherein the composition comprises free fluoride ions in a range of about 400 ppm to 1500 ppm.

5. The composition according to claim 1, wherein the composition comprises about 900 ppm free fluoride.

6. The composition according to claim 1, wherein the composition further comprises a dentally acceptable polishing material and a surfactant.

7. The composition according to claim 1, wherein the composition is selected from the group consisting of toothpaste; tooth gel; tooth powder; dental creme; dentifrice; troche; chewing gum; gingival massage creme; gargle tablet; and dental restorative.

* * * * *